(12) United States Patent
Parthasarathy et al.

(10) Patent No.: US 8,198,317 B2
(45) Date of Patent: Jun. 12, 2012

US008198317B2

(54) METHYLENEDIOXY PHENOLIC COMPOUNDS AND THEIR USE TO TREAT DISEASE

(75) Inventors: Sampath Parthasarathy, Columbus, OH (US); Sanjay Rajagopalan, Columbus, OH (US); Desikan Rajagopal, Columbus, OH (US)

(73) Assignees: The Ohio State University Research Foundation, Columbus, OH (US); Invasc Therapeutic, inc., Tucker, GA (US)

( * ) Notice: Subject to any disclaimer, the term of this patent is extended or adjusted under 35 U.S.C. 154(b) by 150 days.

(21) Appl. No.: 12/536,295

(22) Filed: Aug. 5, 2009

(65) Prior Publication Data
US 2010/0035849 A1    Feb. 11, 2010

Related U.S. Application Data

(60) Provisional application No. 61/086,425, filed on Aug. 5, 2008.

(51) Int. Cl.
*A61K 31/385* (2006.01)
*C07D 409/12* (2006.01)
(52) U.S. Cl. .......................... 514/440; 549/37
(58) Field of Classification Search .................. 514/440; 549/37
See application file for complete search history.

(56) References Cited

FOREIGN PATENT DOCUMENTS
EP          1229034 A1    8/2002
WO        02060896 A1    8/2002

OTHER PUBLICATIONS

Arnold, Richard T., et al, Orientation in the 1,3-Benzodioxole Series, Journal of the American Chemical Society, vol. 67, pp. 1797-1798, 1945.
Bhaskaran, S., et al. Inhibition of atherosclerosis in low-density lipoprotein receptor-negative mice by sesame oil. J Med Food. 2006 Winter; 9 (4):487-90.
Orphanos, D.G., et al., Preparation of 3,-4-Methylenedioxy-and 3,4-Dimethoxy-6-Aminophenol, Canadian Journal of Chemistry, vol. 44, pp. 1875-1879, 1966.
Santanam, N, Parthasarathy S. Aspirin is a substrate for paraoxonase-like activity: Implications in atherosclerosis. Atherosclerosis. 191, 272-275, 2007.
Thompson, R.B., et al, Some Derivatives of Hydroxyhydroquinone as Antioxidants, Journal of the American Oil Chemists' Society, Vo. 33, pp. 414-416, 1956.
Ye, Yue Qi, et al., First Total Synthesis of Vialinin A, a Novel and Extremely Potent Inhibitor of TNF-a Production, Organic Letters, vol. 9, No. 21, pp. 4131-4134, 2007.
Zhang, W., et al. Alpha-lipoic Acid attenuates LPS-induced inflammatory responses by activating the phosphoinisitide 3-kinase/Akt signaling pathway, PNAS, 104, 4077-4082, 2007X.
PCT International Search Report, PCT/US2009/052893, filed Aug. 5, 2009.
PCT Written Opinion of the International Searching Authority, PCT/US2009/052893, filed Aug. 5, 2009.

*Primary Examiner* — Taofiq A Solola
(74) *Attorney, Agent, or Firm* — MacMillan, Sobanski & Todd, LLC

(57) ABSTRACT

The present invention provides novel methylenedioxy phenolic compounds and their derivatives, methods of making them and methods of using them to treat or prevent cardiovascular disease, vascular disease and/or inflammatory disease, as well as Type I and Type II Diabetes and Dyslipidemia patients at risk for hypertension, stroke, cardiovascular and renal disease.

45 Claims, 19 Drawing Sheets

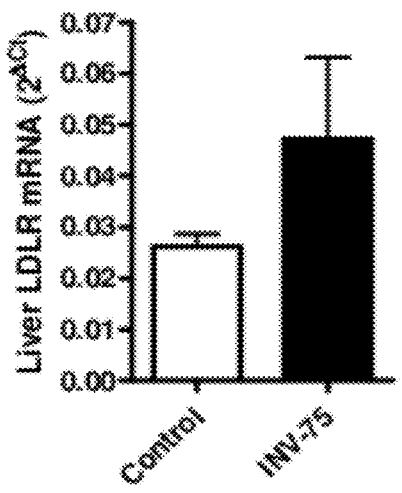
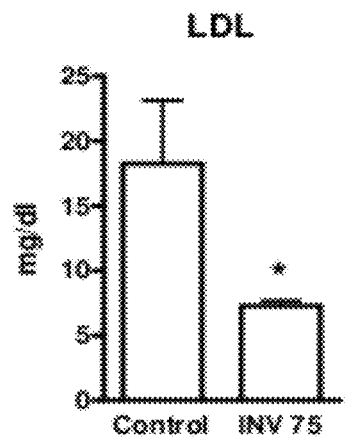
FIGURE 26　　　　　　　　　　　　　　FIGURE 27
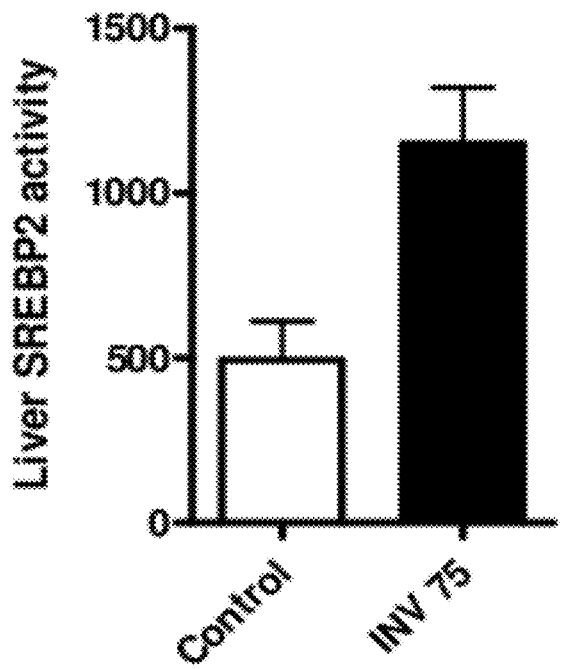
FIGURE 28

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Artificial sequence = synthetic construct

<400> SEQUENCE: 1
gcctgaggtc cagttctgtg                                              20

<210> SEQ ID NO 2
<211> LENGTH: 20
<212> TYPE: DNA
<213> ORGANISM: Artificial Sequence
<220> FEATURE:
```

<223> OTHER INFORMATION: Artificial sequence = synthetic construct

<400> SEQUENCE: 2
gcggacacag ctctcagtag                                           20

<210> SEQ ID NO 3
<211> LENGTH: 20
<212> TYPE: DNA
<213> ORGANISM: Artificial Sequence
<220> FEATURE:
<223> OTHER INFORMATION: Artificial sequence = synthetic construct

<400> SEQUENCE: 3
gcctggagaa agctgctaag                                           20

<210> SEQ ID NO 4
<211> LENGTH: 20
<212> TYPE: DNA
<213> ORGANISM: Artificial Sequence
<220> FEATURE:
<223> OTHER INFORMATION: Artificial sequence = synthetic construct

<400> SEQUENCE: 4
ccagcatcga aggtagagga                                           20

<210> SEQ ID NO 5
<211> LENGTH: 21
<212> TYPE: DNA
<213> ORGANISM: Artificial Sequence
<220> FEATURE:
<223> OTHER INFORMATION: Artificial sequence = synthetic construct

<400> SEQUENCE: 5
tgccgagcta aattacatat c                                         21

<210> SEQ ID NO 6
<211> LENGTH: 20
<212> TYPE: DNA
<213> ORGANISM: Artificial Sequence
<220> FEATURE:
<223> OTHER INFORMATION: Artificial sequence = synthetic construct

<400> SEQUENCE: 6
tcattgtcac agagccacct                                           20

<210> SEQ ID NO 7
<211> LENGTH: 20
<212> TYPE: DNA
<213> ORGANISM: Artificial Sequence
<220> FEATURE:
<223> OTHER INFORMATION: Artificial sequence = synthetic construct

<400> SEQUENCE: 7
cggaccagaa agactggact                                           20

<210> SEQ ID NO 8
<211> LENGTH: 21
<212> TYPE: DNA
<213> ORGANISM: Artificial Sequence
<220> FEATURE:
<223> OTHER INFORMATION: Artificial sequence = synthetic construct

<400> SEQUENCE: 8
gttcctcaca tggtgctgga c                                         21

<210> SEQ ID NO 9

```
<211> LENGTH: 20
<212> TYPE: DNA
<213> ORGANISM: Artificial Sequence
<220> FEATURE:
<223> OTHER INFORMATION: Artificial sequence = synthetic construct

<400> SEQUENCE: 9
gctcagaagg agccgagtta                                               20

<210> SEQ ID NO 10
<211> LENGTH: 20
<212> TYPE: DNA
<213> ORGANISM: Artificial Sequence
<220> FEATURE:
<223> OTHER INFORMATION: Artificial sequence = synthetic construct

<400> SEQUENCE: 10
ttaccatgac tgccacagga                                               20

<210> SEQ ID NO 11
<211> LENGTH: 18
<212> TYPE: DNA
<213> ORGANISM: Artificial Sequence
<220> FEATURE:
<223> OTHER INFORMATION: Artificial sequence = synthetic construct

<400> SEQUENCE: 11
agcaccaagt gtcccaaa                                                 18

<210> SEQ ID NO 12
<211> LENGTH: 20
<212> TYPE: DNA
<213> ORGANISM: Artificial Sequence
<220> FEATURE:
<223> OTHER INFORMATION: Artificial sequence = synthetic construct

<400> SEQUENCE: 12
tgtgttcttg ggttgtggaa                                               20
```

METHYLENEDIOXY PHENOLIC COMPOUNDS AND THEIR USE TO TREAT DISEASE

PRIOR RELATED APPLICATIONS

This application claims benefit of priority from U.S. Provisional Patent Application No. 61/086,425 filed Aug. 5, 2008 which is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing, created on Aug. 5, 2009, with a file named "604__29993 Sequence_Listing OSURF-08051.txt", and having a size of 3 kilobytes, and is filed concurrently with the specification. The sequence listing contained in this ASCII formatted document is part of the specification and is herein incorporated by reference in its entirety.

FIELD OF THE INVENTION

Novel methylenedioxy phenolic-based compounds and their derivatives are presented together with methods of making them and methods of using them to treat or prevent vascular disease, cardiovascular disease, inflammatory disease, diabetic vascular disease and related conditions.

BACKGROUND OF THE INVENTION

Cardiovascular disease or heart disease is the number one killer around the world and the associated risk factors are on the increase globally. For example, cardiovascular and metabolic diseases such as diabetes, where there is an anticipated increase of over 40% in the incidence rate around the world by the year 2025, metabolic syndrome, hypertension and dyslipidemia are the leading causes of morbidity and mortality. In addition, recent studies indicate that even hitherto protected subsets such as younger women are becoming increasingly vulnerable to heart disease. The global need for new cardiovascular drugs is therefore, steadily increasing.

Cardiovascular disease secondary to atherosclerosis is not a single disease. There are multiple risk factors associated with the disease. These include diabetes, hypertension, dyslipidemia, smoking, thrombophilia (increased clotting tendency or thrombosis) and positive family history. Often, patients have multiple risk factors and are treated with multiple drugs. While combination therapy has been proven effective, often drug-to-drug interactions, the inconvenience of multiple daily dosing, etc. as well as undiagnosed risk factors, make it necessary to take a multipronged approach.

To date, many of these risk factors have been treated as separate diseases although there are numerous commonalities among them. For example, the drugs against hypertension have little no effect on diabetes and vice versa. Recent studies have suggested that many of these diseases (risk factors) have common features such as an elevated inflammatory and oxidative stress. In addition, altered endothelial function is a common clinically significant observation associated with almost all these risk factors.

The present invention provides for the use of these novel methylenedioxy phenolic compounds and their derivatives in the preparation of a medicament useful to treat, prevent or delay the onset and progression of cardiovascular disease, vascular disease and/or inflammatory disease, as well as Type I and Type II Diabetes and Dyslipidemia patients at risk for hypertension, stroke, cardiovascular and renal disease.

It would be desirable to have one or more drugs that could treat or prevent one or more facets or symptoms of a cardiovascular disease, inflammatory disease, diabetic vascular disease or a related disorder.

SUMMARY OF THE INVENTION

The present invention substantially mitigates these problems by providing novel methylenedioxy phenolic compounds and their derivatives, methods of making them and methods of using them to treat, prevent or delay the onset and progression of cardiovascular disease, vascular disease and/or inflammatory disease, as well as Type I and Type II Diabetes and Dyslipidemia patients at risk for hypertension, stroke, cardiovascular and renal disease.

These methylenedioxy phenolic compounds and their derivatives possess the ability to prevent the progression of atherosclerosis. Accordingly, these compounds are useful in preventing accumulation of plaque and delaying or preventing atherosclerosis in individuals such as those at risk for atherosclerosis. Since these compounds are useful in preventing accumulation of plaque and delaying or preventing atherosclerosis, they may be administered to prevent or reduce the occurrence of heart attacks, strokes, death, peripheral arterial disease and revascularization events (coronary artery bypass graft surgery or lower extremity bypass surgery).

These methylenedioxy phenolic compounds and their derivatives possess anti-inflammatory properties, as evidenced at least by the effects on prevention of activation of the transcription factor nuclear factor-kappa B (NFkB). Accordingly, these compounds are useful in various inflammatory disorders including but not limited to atherosclerosis, diabetes, inflammatory arthritis (rheumatoid arthritis, psoriatic arthritis), hypertension and aging. For example, these compounds can be combined with an acceptable carrier and administered to patient who has recently sustained a heart attack or stroke or has undergone a recent percutaneous intervention to the coronary or peripheral arterial vessels. These compositions are also useful for administration to patients receiving stents in coronary arteries and peripheral arteries.

These methylenedioxy phenolic compounds and their derivatives will have protective effects in diabetes and in preventing diabetic vascular disease including diabetic heart disease, diabetic kidney disease and diabetic cerebrovascular disease, in view of their effects in improving vascular insulin sensitivity.

These methylenedioxy phenolic compounds and their derivatives also affect the transcription factor sterol regulator and binding protein-2 (SREBP-2). These compounds act as post-transcriptional activators of SREBP-2 and represent a novel class of selective activators of SREBP-2. The increase in SREBP-2 increases low density lipoprotein receptor (LDLR) and lowers LDL cholesterol levels. Accordingly, these compounds may be used to treat hyperlipidemia associated with elevated LDL levels such as heterozygous familial hypercholesterolemia and homozygous familial hypercholesterolemia, combined hyperlipidemia, elevations in very low density lipoprotein (VLDL) cholesterol and in diabetic dyslipidemia.

In light of the substantial benefit provided by these methylenedioxy phenolic compounds and their derivatives in atherosclerosis and inflammation, they may also be administered in combination with other therapies known to one of ordinary skill in the art to be effective in atherosclerosis and inflammation including but not limited to HMG-CoA reductase inhibitors, angiotensin converting enzyme inhibitors (ACEI), fat uptake inhibitors, angiotensin receptor blockers, peroxisome proliferation activator receptor-alpha (PPAR-alpha) and PPAR-gamma agonists, acetylsalicylic acid, cholesteryl ester transfer protein (CETP) inhibitors and beta-blockers.

The methylenedioxy phenolic compounds and their derivatives of the present invention are combined with a pharmaceutically acceptable carrier to form compositions for administration to an animal or a human. These compositions are used to treat or prevent vascular disease, cardiovascular disease, inflammatory disease, diabetic vascular disease or a related disorder and many of their underlying risk factors. These compositions may be administered alone or together with another therapeutic compound. Such administration of the compositions of the present invention and one or more additional therapeutic compound may occur separately. Alternatively, the compositions of the present invention and one or more additional therapeutic compound may be combined in one administration or delivery method, for example in one capsule, one caplet or one intravenous administration.

These and other objects, features and advantages of the present invention will become apparent after a review of the following detailed description of the disclosed embodiments and claims.

feeding. Post-HFC=values obtained after initiation of high fat chow but before treatment with drug. Post INV-75/controls represent values following treatment with control of INV-75. N=4-5/group. The total cholesterol values were no different between the groups. All animals were fed a high fat chow. The high levels of total cholesterol in this model likely prevented observation of significant effects on total cholesterol.

Figure 14A:
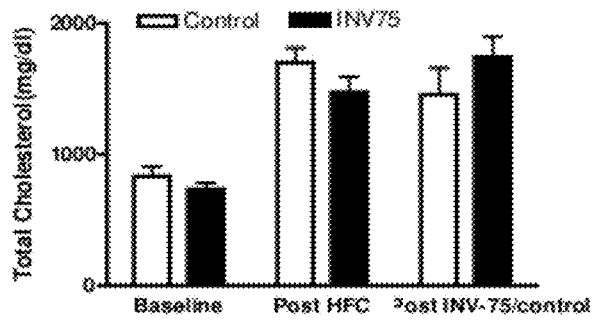
FIG. 14A is a graph representing the effect of INV-75 on total cholesterol in the WHHL rabbit versus control. The baseline values were obtained prior to high fat chow (HFC)
Figure 14B:
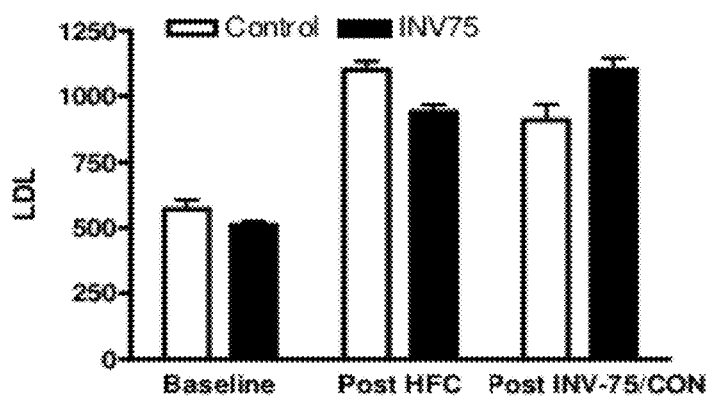

FIG. 14B is a graph representing the effect of INV-75 on controlling LDL cholesterol in the WHHL rabbit versus control intervention. The baseline values were obtained prior to high fat chow feeding. Post-HFC=values obtained after initiation of high fat chow but before treatment with drug. Post INV-75/controls represent values following treatment with control of INV-75. N=4-5/group. The LDL cholesterol values were no different between the groups. All animals were fed a high fat chow. The high levels of LDL cholesterol in this model likely prevented observation of significant effects on total cholesterol.

Figure 15:
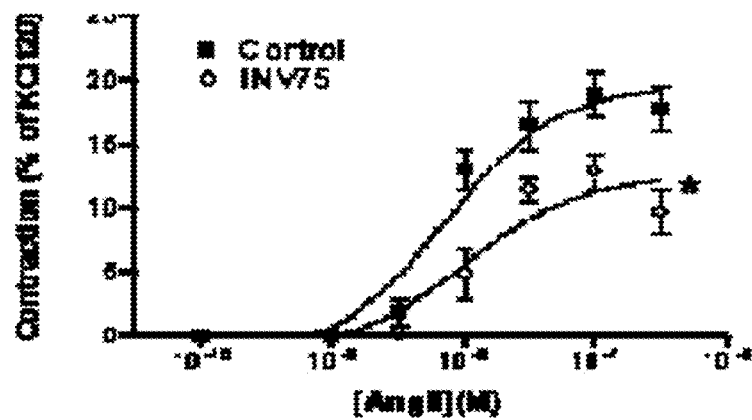

FIG. 15 is a graph showing contraction by vasoconstrictor angiotensin II (AngII) (% of Potassium Chloride, KCl, 120 mM) for control animals and INV-75 treated WHHL animals *$p<0.05$, One way ANOVA, N=4-5/group. All animals were fed high fat diet.

Figure 16:
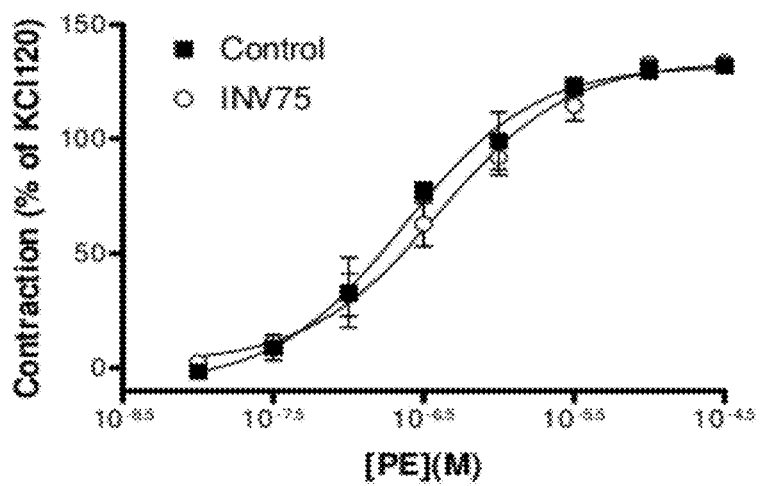

FIG. 16 is a graph showing % of constriction to phenylephrine in the thoracic aorta expressed as a percentage of peak constriction to Potassium Chloride (KCl, 120 mM) for control and INV-75 treated WHHL animals N=4-5/group. All animals were fed high fat diet.

Figure 17:
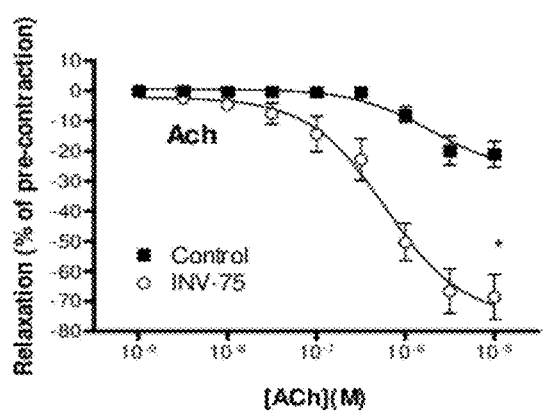

FIG. 17 is a graph showing the relaxation by acetylcholine (Ach) (% of pre-contraction by 1 µM phenylephrine, PE) in the thoracic aortic ring segments of control animals vs. INV-75 treated animals. One way ANOVA for peak relaxation with INV-75 vs. controls (n=5/group). ***$p<0.001$ versus controls for peak relaxation by acetylcholine. The thoracic aorta was obtained from WHHL rabbits at sacrifice at the end of treatment with INV-75 or control intervention. All animals received high fat diet.

Figure 18:
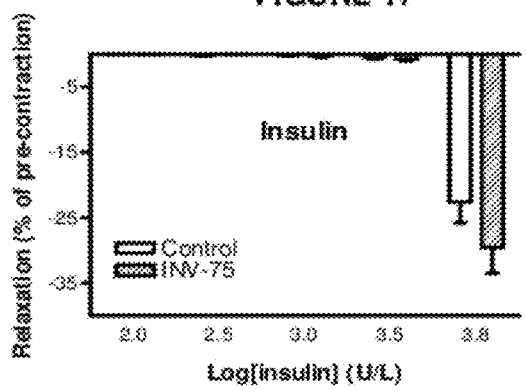

FIG. 18 is a graph showing the relaxation of tone in thoracic aortic ring segments by insulin (% of pre-contraction by 1 µM phenylephrine, PE) for control animals and INV-75 treated animals.

Figure 19:
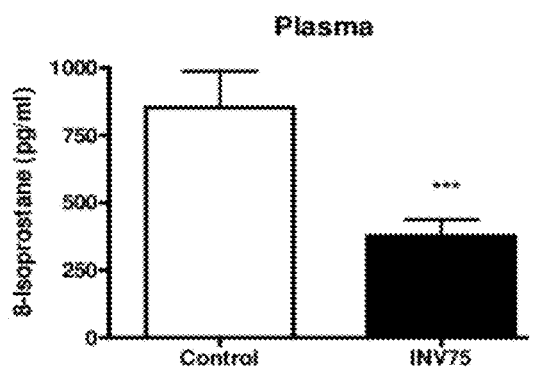
Figure 20:
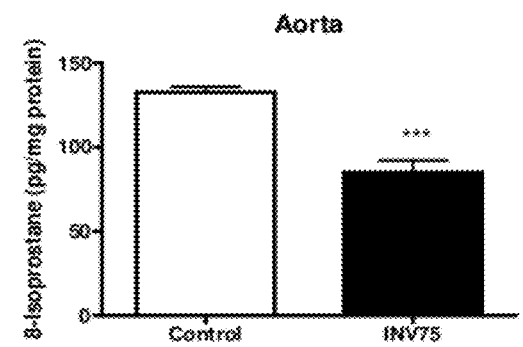
Figure 21:
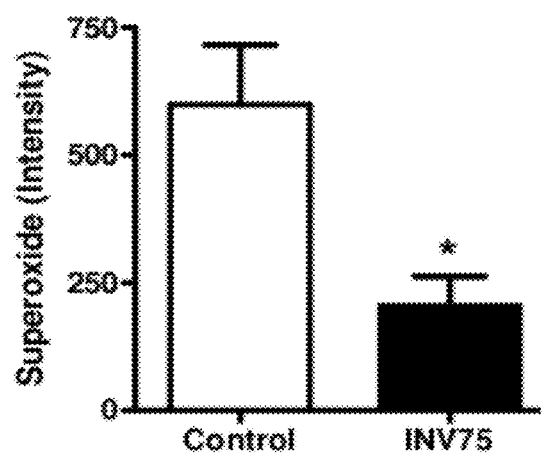

FIG. 19 is a graph showing oxidative stress in plasma, 8-epi Prostaglandin F2α (8-Isoprostane) Enzyme Linked Immunoassay of rabbit plasma as a measure of basal levels of oxidative stress in control and INV-75 treated WHHL rabbits at the end of treatment. N=4-5 rabbits/group. **$p<0.001$ vs. controls by Students' t test adjusted by Bonferroni correction FIG. 20 is a graph showing oxidative stress in the thoracic aorta of control animals vs. INV-75 treated WHHL rabbits. 8-epi Prostaglandin F2α (8-Isoprostane) Enzyme Linked Immunoassay of aortic homogenates as a measure of oxidative stress in control and INV-75 treated WHHL rabbits at the end of treatment. N=4-5 rabbits/group. **$p<0.001$ vs. controls by students' t test adjusted by Bonferroni correction FIG. 21 is a graph showing the effect of INV-75 or control on basal in-situ super oxide production on Watanabe Heritable Hyperlipidemic Rabbit (WHHL) aorta sections, quantified by dihydroethidium (DHE) staining, *, $p<0.01$ for INV-75 compared to control by Student's t test adjusted by Bonferroni correction.

Figure 22:
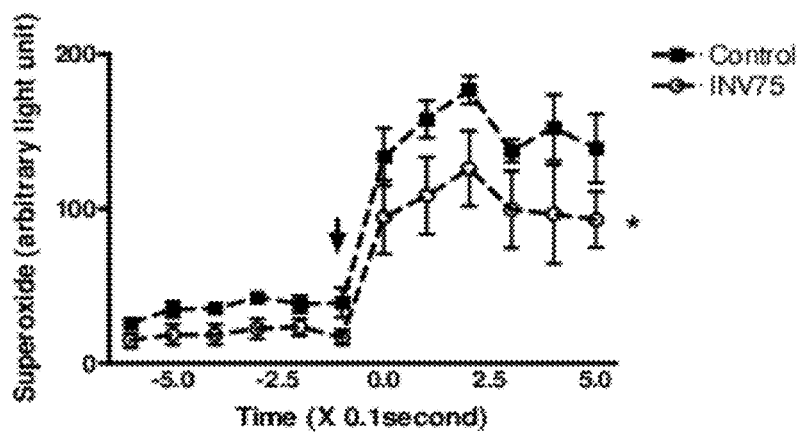

FIG. 22 is a graph showing basal and stimulated superoxide production in response to the agonist NADPH in aortic tissue lysates from Watanabe Heritable Hyperlipidemic Rabbit (WHHL) subjected to INV-75 or control intervention, analyzed by Lucigenin chemiluminescence assay. The arrow indicates the addition of NADPH (100 mM); n=5/group. *, $p<0.05$ vs. control animals by Student's t test adjusted by Bonferroni correction. All animals were fed high fat diet.

Figure 23:
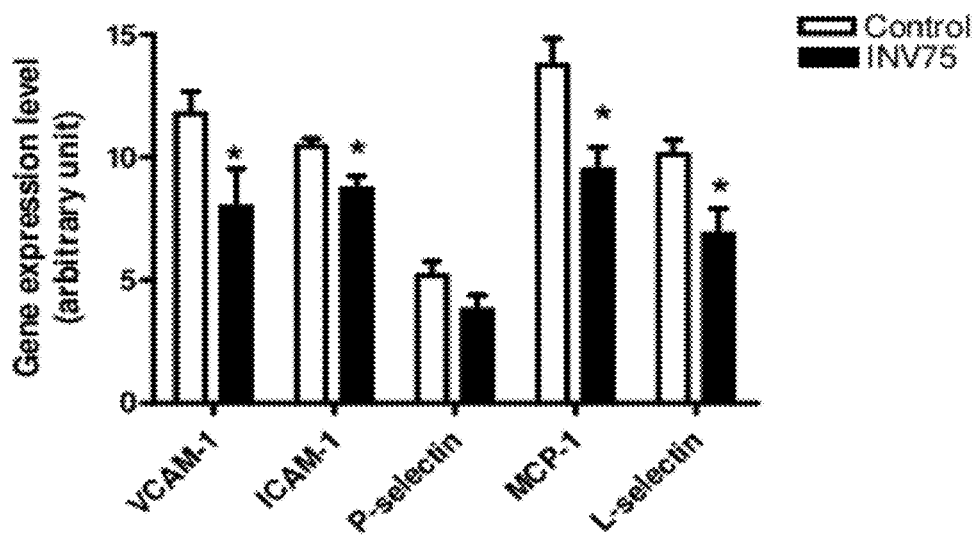

FIG. 23 is a graph showing gene expression level to study the VCAM-1, ICAM-1, P-selectin, MCP-1 and L-Selectin as inflammation markers. Total RNA was prepared from thoracic aorta of WHHL rabbits subjected to INV-75 or controls. The mRNA expression level of pro-inflammatory genes was analyzed by real-time PCR. *, $p<0.05$; Student's t test adjusted by Bonferroni correction. All animals were fed high fat diet.

Figure 24:
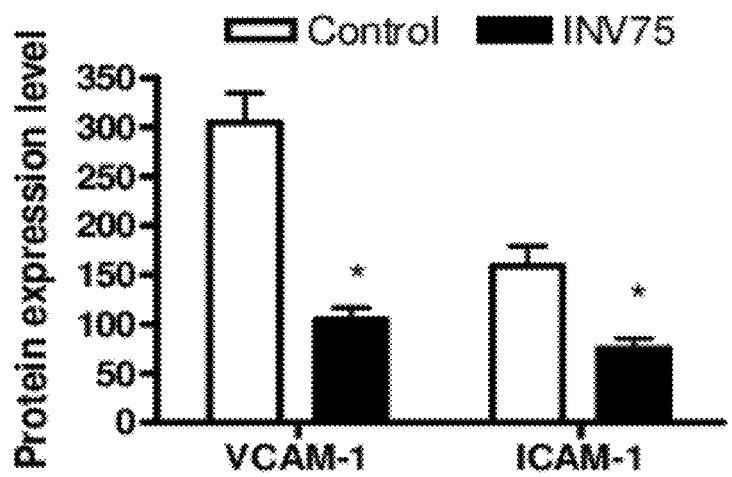

FIG. 24 is a graph showing effect of INV-75 and control intervention on VCAM-1 and ICAM-1 expression in WHHL rabbits. The protein expression level of VCAM-1 and ICAM-1 was analyzed by Western analysis. *, $p<0.05$; Students' t test adjusted by Bonferroni correction. All animals were fed high fat diet.

Figure 25:
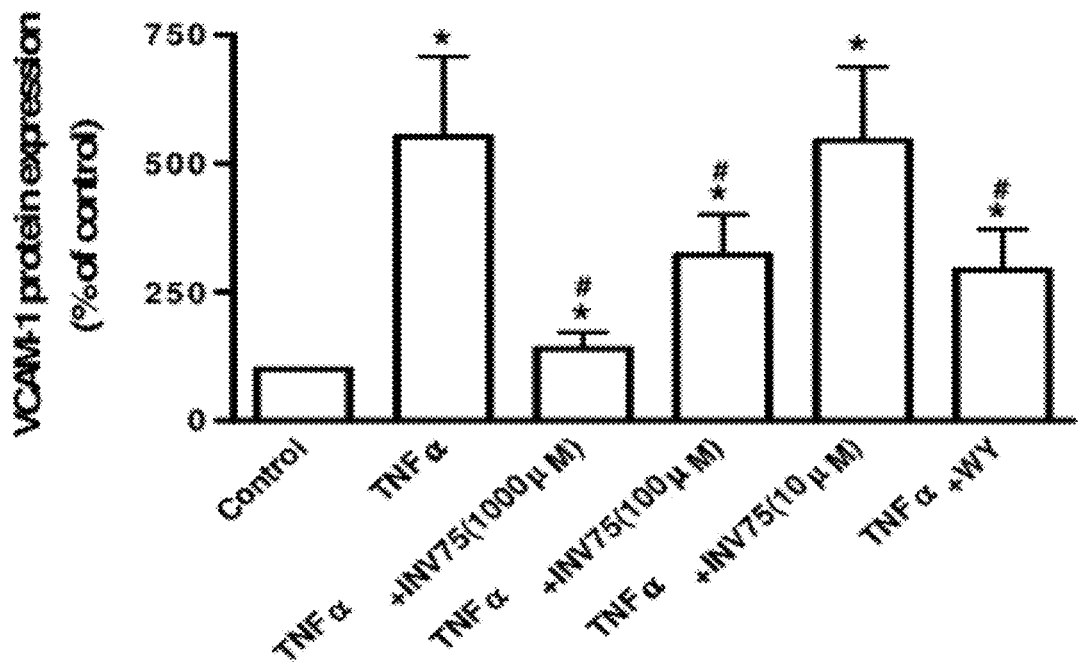

FIG. 25 is a graph showing VCAM-1 protein expression level as a cellular correlate of inflammation. INV-75 inhibits TNFα induced VCAM-1 expression in HUVECs. HUVECs were pretreated with vehicle, INV75, or WY-14643 for 2 hours, and then treated with TNFα for 4 hours. VCAM-1 expression was analyzed by Western blot. A representative and summary of three independent experiments are presented. *, $p<0.05$ vs control; #, $p<0.05$ vs TNFα.

FIG. 26 is a graph showing the effect of INV-75 on liver LDLR mRNA expression in C57BL/6 mice on normal chow treated for 2 weeks with INV-75 or control, measured with RT-PCR. The comparison of results with control and the INV 75 treated group.

FIG. 27 is a graph showing the effect of INV-75 in lowering LDL level in C57BL/6 mice treated for 2 weeks with INV-75 or control *, $p<0.01$ one way ANOVA.

FIG. 28 is a graph showing the effect of INV-75 on liver SREBP2 in C57BL/6 mice on normal chow treated for 2 weeks with INV-75 or control, measured by EMSA.

Figure 29:
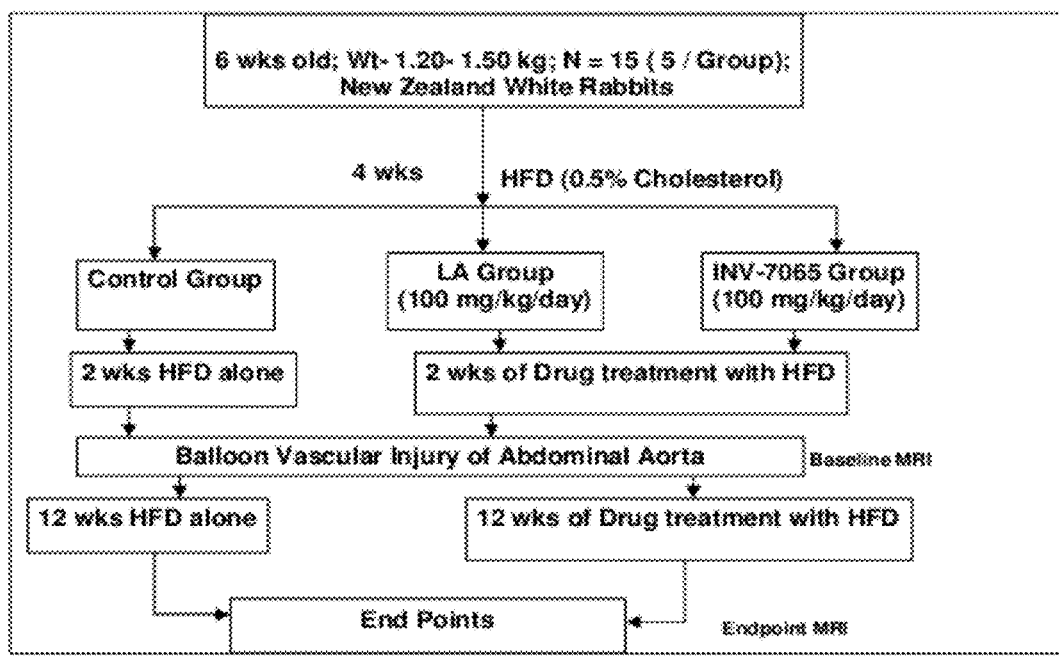

FIG. 29 is a schematic illustration of in vivo experimental protocol used to test the effects of INV-7065 in atherosclerosis in a New Zealand White (NZW) Rabbit model.

Figure 30A:
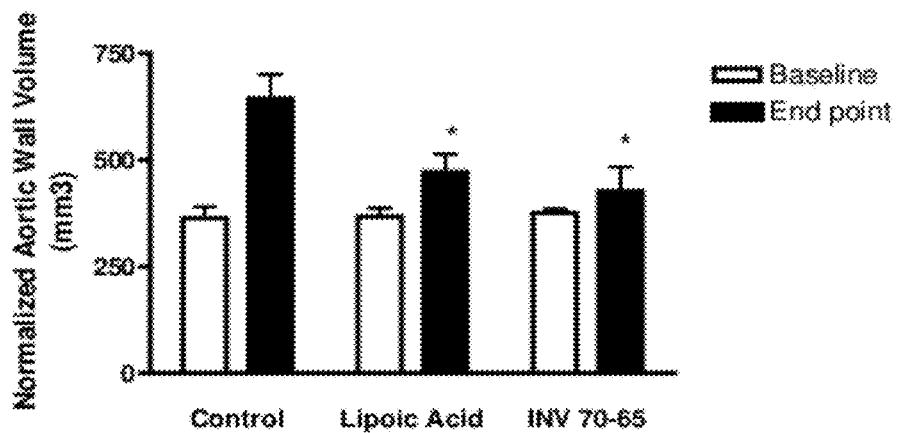

FIG. 30A is a bar graph representing summary of MRI studies indicating decrease in atherosclerosis burden in high fat chow fed New Zealand White (NZW) rabbits treated with INV-7065 lipoic acid treated and control interventions. *$p<0.05$, One way ANOVA vs. control end-point values. (n=4-5/group).

Figure 30B:
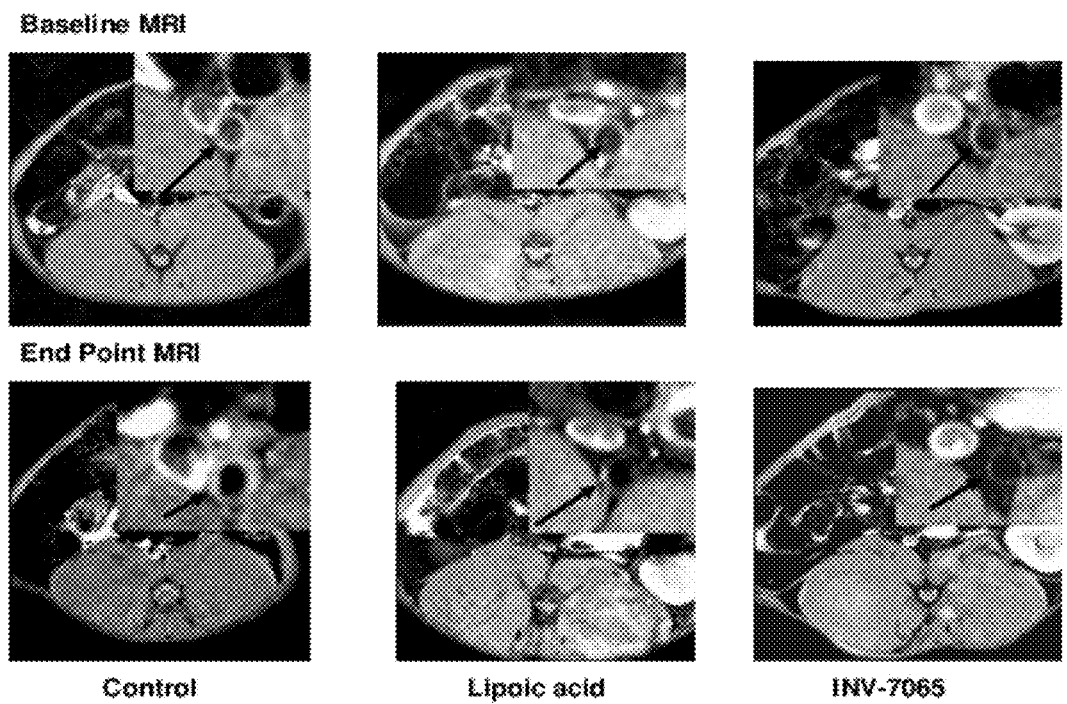

FIG. 30B shows in vivo MRI images obtained following administration of Gadolinium contrast at two different time points, baseline (A) and endpoint (B) (1 wk and 12 wks after balloon denudation surgery respectively). A representative image from each group is presented. Pre contrast abdominal aortic imaging shows INV-7065 decreases contrast opacification of aorta in New Zealand White (NZW) rabbits compared to control group or lipoic acid treatment after 12 wks of treatment in balloon denuded animals. All animals were fed high fat diet.

Figure 31A:
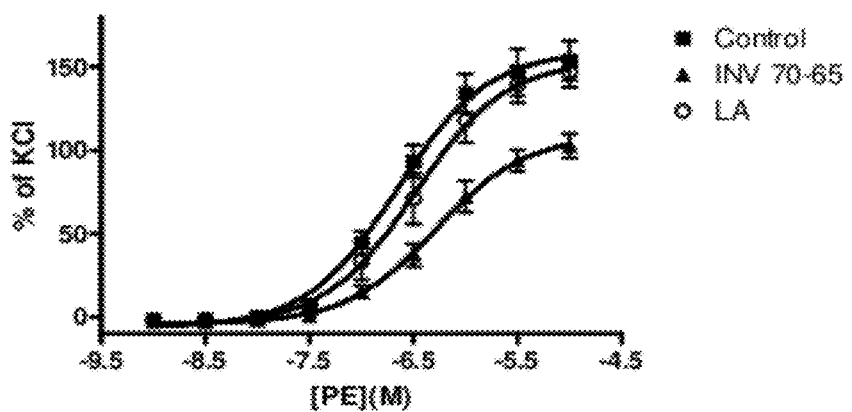

FIG. 31A is a graph showing % of constriction to Potassium Chloride (KCl, 120 mM) for control animals and INV-7065 and lipoic acid treated animals. Phenylephrine (PE) dose response. After total 14 weeks of treatment with INV-7065, lipoic acid or control (n=4-5/group), rabbit were sacrificed and thoracic aortic segments were mounted on myograph chamber. After equilibration at a baseline tone of 30 mN for 2 hours, aortic segments were constricted by various concentrations of PE. The constriction is expressed in relationship to maximum constriction with potassium chloride. *, $p<0.01$ versus lipoic acid or control NZW rabbits by one-way ANOVA. All animals were fed high fat diet.

Figure 31B:
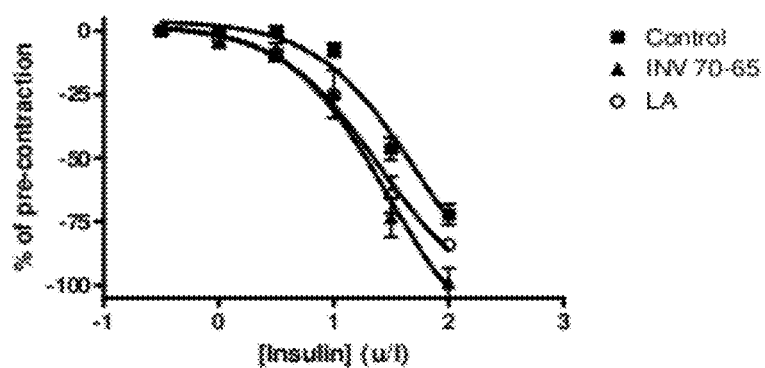

FIG. 31B is a graph showing vascular relaxation response to insulin, thoracic aortic segments in New Zealand White rabbits treated with INV-7065, lipoic acid or controls. Aortic segments were pre-contracted by PE (0.3 μM) and relaxation response to insulin studied. *, p<0.01 versus lipoic acid or control NZW rabbits by one-way ANOVA. (n=4-5/group).

Figure 31C:
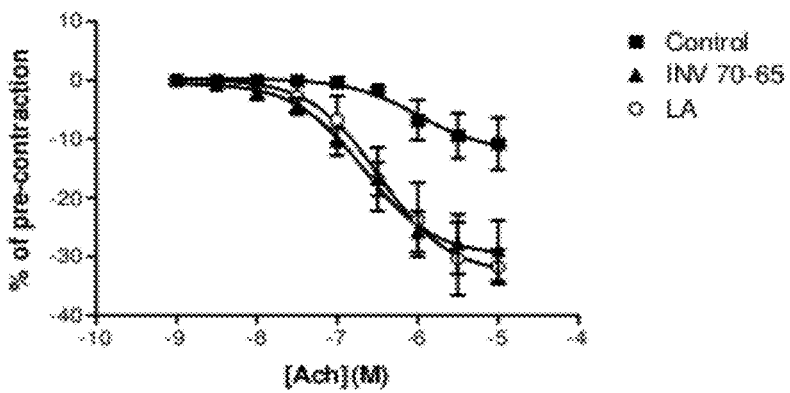

FIG. 31C is a graph showing vascular relaxation response to acetylcholine (% of pre-contraction by phenylephrine PE (0.3 μM) in control, INV-7065 and lipoic acid treated animals as described in FIG. 31b. *, p<0.01 for lipoic acid and INV-7065 versus control NZW rabbits, by one-way ANOVA. Responses between lipoic acid and INV-7065 were no different. (n=4-5/group).

Figure 31D:
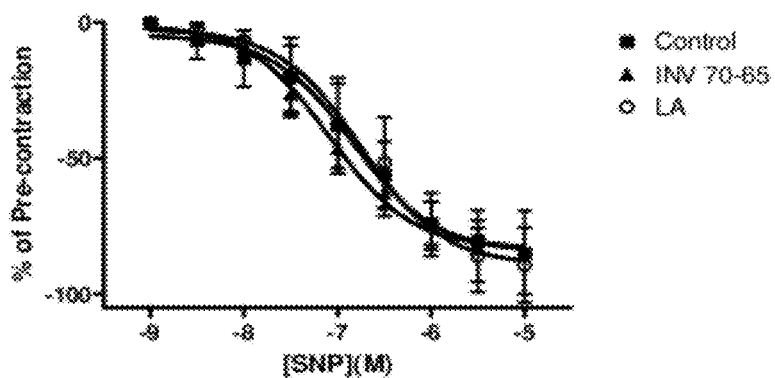

FIG. 31D is a graph showing relaxation by sodium nitroprusside (SNP) (% of pre-contraction by phenylephrine PE (0.3 μM)) in control, INV-7065 and lipoic acid treated New Zealand White rabbits fed high fat diet as described in FIG. 31B. (n=4-5/group).

Figure 32A:
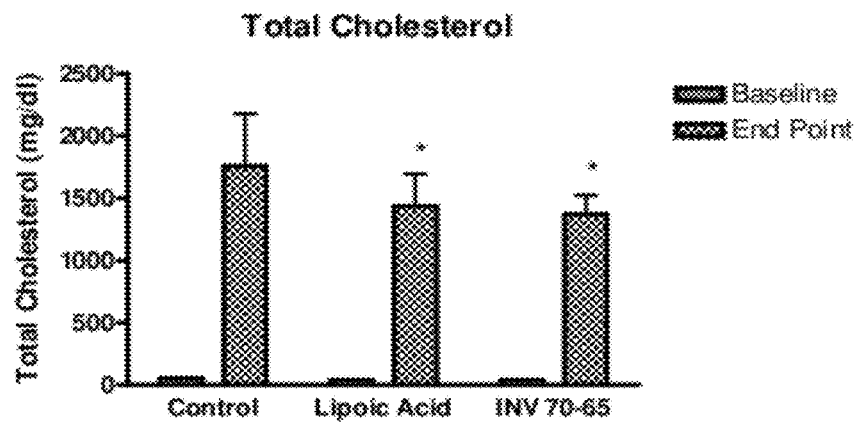

FIG. 32A is a graph showing the effect of INV-7065 and lipoic acid on total cholesterol (TC) in New Zealand White (NZW) rabbits fed high fat diet supplemented with INV-7065, lipoic acid or control (n=4-5/group).

Compare to Normal Control.

In FIG. 32A and also in FIGS. 32B, 32C, 32D and 32E, a one way analysis of variance (ANOVA) statistical test was used, with the p value <0.05 indicated by *.

Figure 32B:
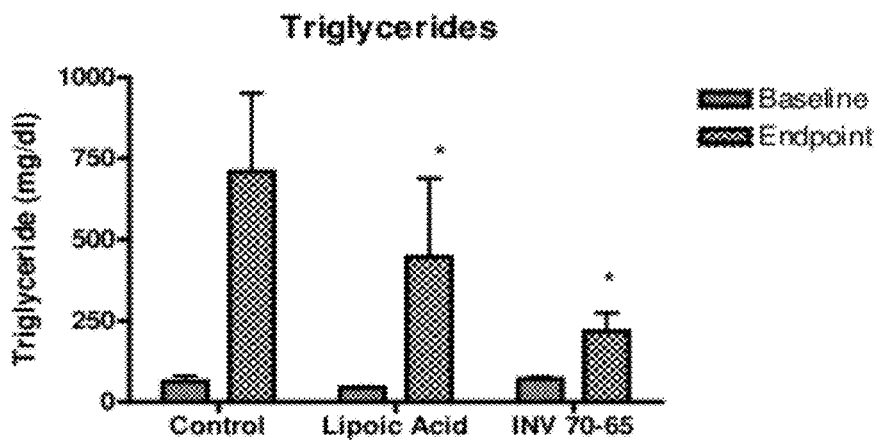

FIG. 32B is a graph showing the effect of INV-7065 and lipoic acid on triglycerides (TG) in New Zealand White (NZW) rabbits fed high fat diet supplemented with INV-7065, lipoic acid or control. Compared to control treated NZW rabbits INV-7065 and Lipoic Acid reduced triglyceride levels. Although there was a trend towards further reduction in triglycerides with INV-7065, these results were not significant.

Figure 32C:
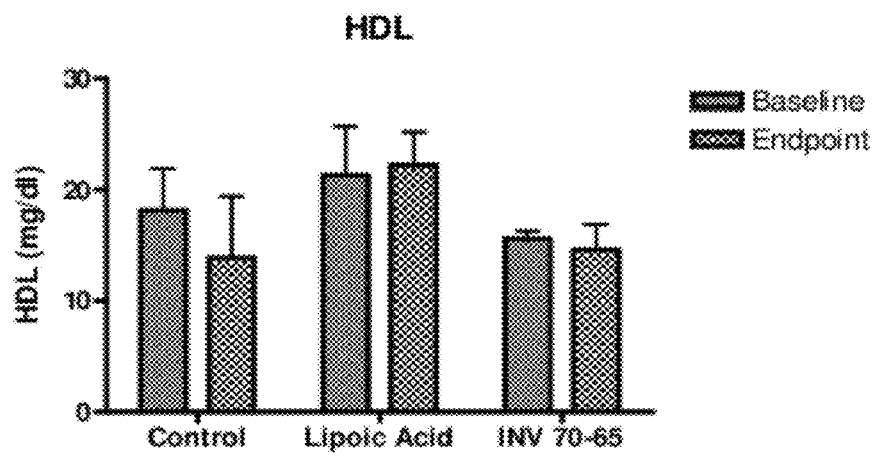

FIG. 32C is a graph showing the effect of INV-7065 and lipoic acid on HDL in New Zealand White (NZW) rabbits fed high fat diet supplemented with INV-7065, lipoic acid or control. There were no differences between baseline and endpoint for both lipoic acid and INV-7065. In the control NZW rabbits fed high fat diet, HDL levels were decreased post high fat chow feeding, although this was not statistically significant.

Figure 32D:
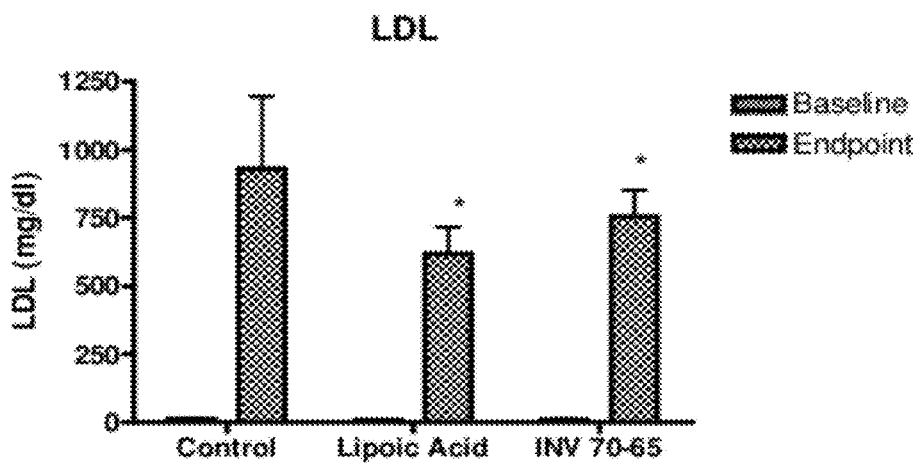

FIG. 32D is a graph showing the effect of INV-7065 and lipoic acid on LDL in New Zealand White (NZW) rabbits fed high fat diet supplemented with INV-7065, lipoic acid or control. Compared to control NZW rabbits, LDL level in lipoic acid and INV-7065 groups were lower.

Figure 32E:
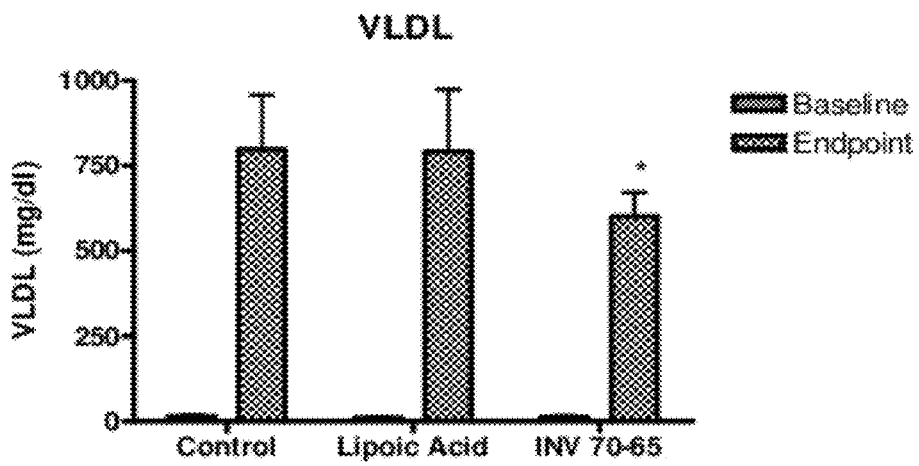

FIG. 32E is a graph showing the effect of INV-7065 and lipoic acid on VLDL in New Zealand White (NZW) rabbits fed high fat diet supplemented with INV-7065, lipoic acid or control (n=4-5/group). Compared to controls and lipoic acid treated rabbits, VLDL level in INV-7065 group was shown to be lowered.

DETAILED DESCRIPTION OF THE INVENTION

The present invention substantially mitigates these problems by providing novel methylenedioxy phenolic compounds and their derivatives, methods of making them and methods of using them to treat, prevent or delay the onset and progression of cardiovascular disease, vascular disease and/or inflammatory disease, as well as Type I and Type II Diabetes and Dyslipidemia patients at risk for hypertension, stroke, cardiovascular and renal disease. The term patient refers to animals and humans herein.

The present invention also provides for the use of these novel methylenedioxy phenolic compounds and their derivatives in the preparation of a medicament useful to treat, prevent or delay the onset and progression of cardiovascular disease, vascular disease and/or inflammatory disease, as well as Type I and Type II Diabetes and Dyslipidemia patients at risk for hypertension, stroke, cardiovascular and renal disease.

Chemical Compositions

In some embodiments, chemical entities of the present invention include compounds described by the following formula I:

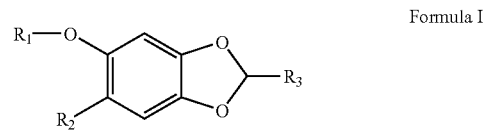

Formula I

Substituents for R1 include but are not limited to the following: hydrogen,

acetyl, ethyl ester, propyl ester, butyl ester, $H_3COC$,

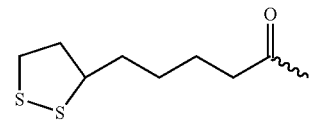

lipoyl,

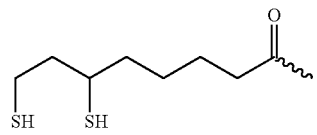

dihydrolipoyl,

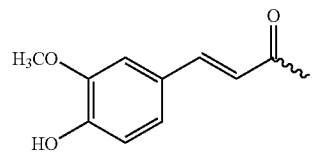

ferulyl, and

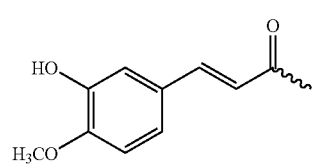

isomeric-ferulyl.

Substituents for R2 may be absent or present and include but are not limited to the following:

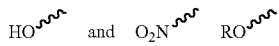

methoxy, -ethoxy, branched alkyl of 1 to 8 carbons, acetyl, lipoyl, dihydrolipoyl, ferulyl and heterocycles such as imidazole, quinaline, isoquinaline, thiazolidinedione, pyrrolidine, piperidine,

carboxyl, methyl ester, ethyl ester, aliphatic amide (1 to 3 carbon), alicyclic amides such as pyrrolidine, piperidine and aromatic amide like aniline, substituted aniline,

amine, alkylated (1 to 3 carbon) amine, amide functional group via lipoic acid, dihydrolipoic acid, aromatic acids like ferulic acid, cinnamic acid, heterocyclic amides derived from proline, substituted proline, pipecolinic acid, and

halogen substitution, fluorine, bromine, chlorine, iodine.

Substituents for R3 may be absent or present and include but are not limited to the following:

alkyl, both normal (1 to 3 carbon) and branched chain (3 to 5 carbon chain), alkyl group having functional group of free carboxylic acid, ester and amide and free hydroxyl and alkylated ether derivatives, alkyl group (1 to 3 carbon chain) having a functional group selected from amine, alkylated amine, both aliphatic, aromatic and heterocyclic amides including imidazole, quinoline, isoquinoline, thiozoline, thiazolidinedione, piperazine, $CH_2CH_2$-thiazolidinedione, $CH_2CH_2CH_3$—CO-lipoyl, $CH_2CH_2$—F, or a halogenated group such as alkyl fluoride (1 to 3 carbon chain).

Specific embodiments of the present invention include but are not limited to the following compounds:

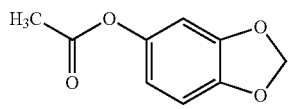

INV-73 = 3,4-methylenedioxy phenyl acetate

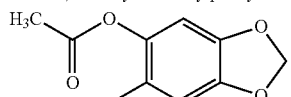

INV-75 = 3,4-methylenedioxy-6-nitrophenyl acetate

-continued

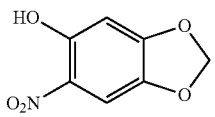

INV-74 = 3,4-methylenedioxy-6-nitrophenol

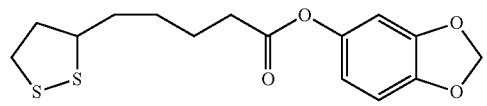

INV-7065 = 3,4-Methylenedioxy phenyl lipoate

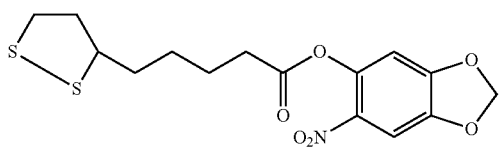

INV-7465 = 3,4-Methylenedioxy 6-nitro phenyl lipoate

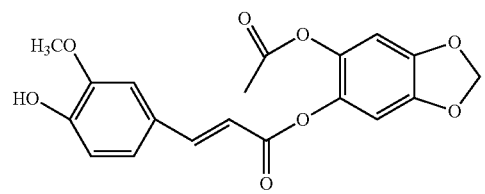

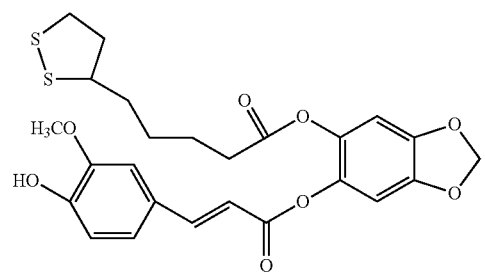

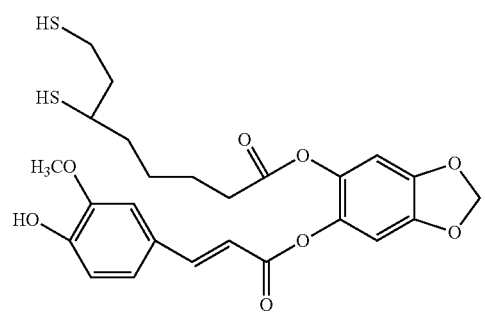

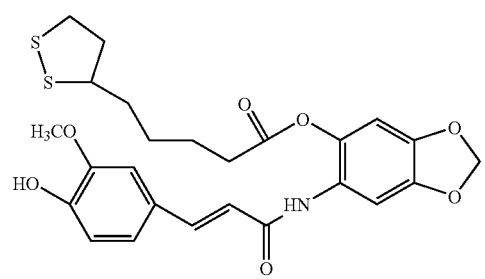

-continued

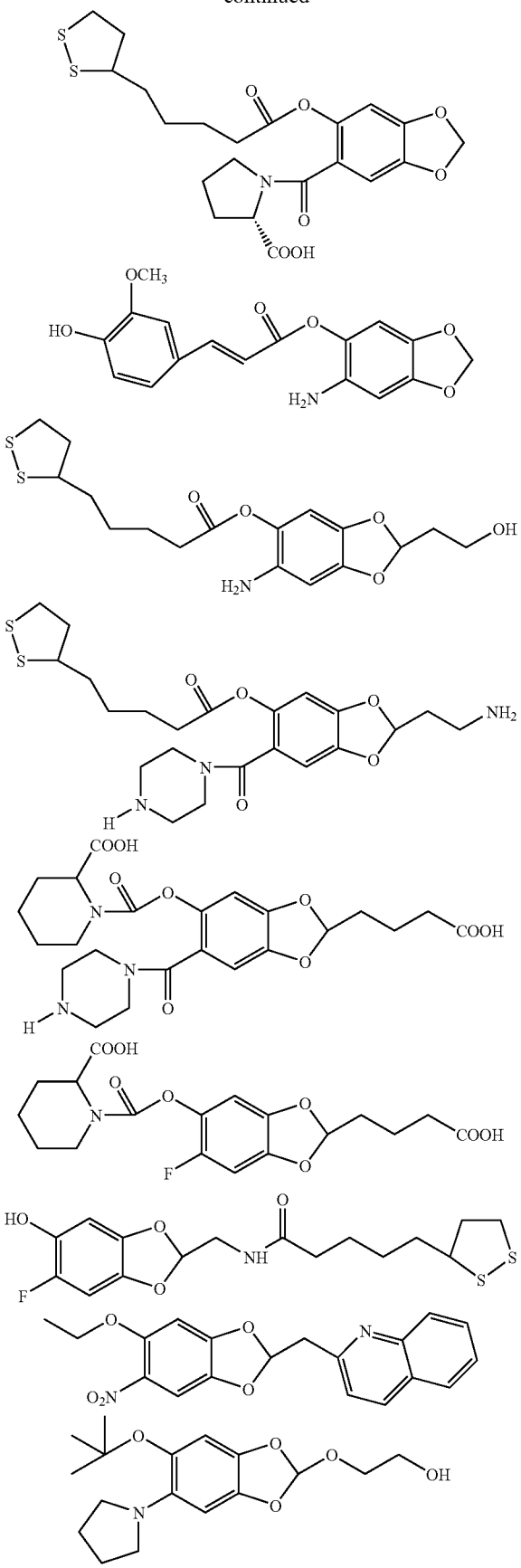
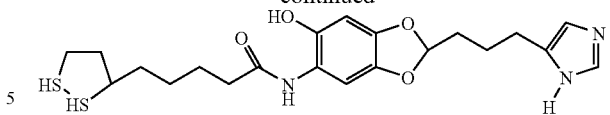

Pharmaceutical Compositions

For administration to an animal or a human, the therapeutic compounds or molecules of the present invention are combined with an acceptable carrier to form a pharmaceutical composition and are administered to the animal or the human. The therapeutic compounds of the present invention may be reconstituted in any pharmaceutically acceptable carrier before use or administration.

Pharmaceutically Acceptable Carriers

Pharmaceutically acceptable carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules described herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Representative Methods of Administration, Formulations and Dosage

The provided therapeutic compounds can be combined with a pharmaceutically acceptable carrier or vehicle for administration to human or animal subjects. In some embodiments, more than therapeutic compound can be combined to form a single preparation. The therapeutic compounds can be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The pharmaceutical compositions provided herein, including those for use in treating disorders, for example cardiovascular disorders, may be administered through, different routes, such as oral, including buccal and sublingual, rectal, parenteral, aerosol, nasal, intramuscular, intraperitoneal, intravascular, intravenous, intraarterial, intraarticular, subcutaneous, intradermal, and topical. They may be administered in different forms, including but not limited to solutions, emulsions and suspensions, microspheres, particles, microparticles, nanoparticles, and liposomes. In one embodiment, therapeutic compounds are combined with an acceptable carrier to form a pharmaceutical composition for oral administration in a pill, capsule or with food.

In another embodiment, it may be desirable to administer the pharmaceutical compositions locally to the area in need of treatment. This maybe achieved by, for example, and not by way of limitation, local or regional infusion or perfusion during surgery, direct perfusion into a vessel, such as an atherosclerotic vessel, topical application (e.g., wound dressing, drug coated stent), injection, catheter, suppository, or implant (e.g., implants formed from porous, non-porous, or gelatinous materials, including membranes, such as silastic membranes or fibers), and the like. In one embodiment, administration can be by direct injection at the site (or former site) of a tissue that is to be treated, such as the heart or the peripheral vasculature. In another embodiment, the pharmaceutical compositions are delivered in a vesicle, in particular liposomes (see, e.g., Langer, *Science* 249:1527-1533, 1990; Treat et al., in *Liposomes in the Therapy of Infectious Disease and Cancer*, Lopez-Berestein and Fidler (eds.), Liss, N.Y., pp. 353-365, 1989). Combinations of administration methods may also be employed such as a systemic or local infusion of a therapeutic compound of the present invention, before, after or during placement of a stent coated with a therapeutic compound of the present invention.

In yet another embodiment, the pharmaceutical compositions can be delivered in a controlled release system. In one embodiment, a pump can be used (see, e.g., *Langer Science* 249:1527-1533, 1990; Sefton *Crit. Rev. Biomed. Eng.* 14:201-240, 1987; Buchwald et al., *Surgery* 88:507-516, 1980; Saudek et al., *N. Engl. J. Med.* 321:574-579, 1989). In another embodiment, polymeric materials can be used (see, e.g., Ranger et al., *Macromol. Sci. Rev. Macromol. Chem.* 23:61-64, 1983; Levy et al., *Science* 228:190-192, 1985; During et al., Ann. Neurol. 25:351-356, 1989; and Howard et al., *J. Neurosurg.* 71:105-112, 1989). Other controlled release systems, such as those discussed in the review by Langer (*Science* 249:1527-1533, 1990), can also be used.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances. An example of such a dosage range is 0.1 to 200 mg/kg body weight in single or divided doses. Other dosage ranges include 1.0 to 150 mg/kg, 1.0 to 100 mg/kg, 5.0 to 100 mg/kg, 10 to 75 mg/kg body weight in single or divided doses. It is to be understood that any dosage within these ranges may be employed.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the subject undergoing therapy.

The pharmaceutical compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. The volume of administration will vary depending on the route of administration. By way of example, intramuscular injections may range from about 0.1 ml to about 1.0 ml. Those of ordinary skill in the art will know appropriate volumes for different routes of administration.

Diseases or Conditions to be Treated

The present invention provides novel methylenedioxy phenolic compounds and their derivatives, methods of making them and methods of using them to treat or prevent vascular disease (including but not limited to cardiovascular disease, cerebrovascular disease, peripheral vascular disease, and diabetic vascular disease), inflammatory disease, or a related disorder and many of their underlying risk factors.

These methylenedioxy phenolic compounds and their derivatives possess the ability to prevent the progression of atherosclerosis. Accordingly, these compounds are useful in preventing accumulation of plaque and delaying or preventing atherosclerosis in individuals such as those at risk for atherosclerosis. Since these compounds are useful in preventing accumulation of plaque and delaying or preventing atherosclerosis, they may be administered to prevent or reduce the occurrence of heart attacks, strokes, peripheral arterial disease and revascularization events (coronary artery bypass graft surgery or lower extremity bypass surgery).

These methylenedioxy phenolic compounds and their derivatives possess anti-inflammatory properties, as evidenced at least by the effects on activation of the transcription factor nuclear factor-kappa B (NFkB). Accordingly, these compounds are useful in various inflammatory disorders including but not limited to atherosclerosis, diabetes, inflammatory arthritis (rheumatoid arthritis, psoriatic arthritis), hypertension and aging. For example, these compounds can be combined with an acceptable carrier and administered to patient who has recently sustained a heart attack or stroke or has undergone a recent percutaneous intervention to the coronary or peripheral arterial vessels. These compositions are also useful for administration to patients receiving stents in coronary arteries and peripheral arteries.

These methylenedioxy phenolic compounds and their derivatives will have protective effects in diabetes and in preventing diabetic vascular disease including diabetic heart disease, diabetic kidney disease and diabetic cerebrovascular disease, in view of their effects in improving vascular insulin sensitivity.

These methylenedioxy phenolic compounds and their derivatives also affect the transcription factor sterol regulator and binding protein-2 (SREBP-2). These compounds act as post-transcriptional activators of SREBP-2 and represent a novel class of selective activators of SREBP-2. The increase in SREBP-2 increases LDLR and lowers LDL cholesterol levels. Accordingly, these compounds may be used to treat hyperlipidemia associated with elevated LDL levels such as heterozygous familial hypercholesterolemia and homozygous familial hypercholesterolemia, combined hyperlipidemia, elevations in VLDL cholesterol and in diabetic dyslipidemia.

Combination Therapy

In light of the substantial benefit provided by these methylenedioxy phenolic compounds and their derivatives in atherosclerosis and inflammation, they may also be administered in combination with other therapies known to one of ordinary skill in the art to be effective in atherosclerosis and inflammation including but not limited to HMG-CoA reductase inhibitors, angiotensin converting enzyme inhibitors (ACEI), fat uptake inhibitors, angiotensin receptor blockers, PPAR-alpha (e.g., Rosiglitazone, Pioglitazone) and PPAR-gamma agonists (Gemfibrozil, Fenofibrate, Bezafibrate), acetylsalicylic acid, cholesteryl ester transfer protein (CETP) inhibitors (Anacetrapib), lipoic acid, and beta-blockers and combinations thereof.

These methylenedioxy phenolic compounds and their derivatives of the present invention may be administered alone or together with another therapeutic compound. Such administration of the compositions of the present invention and one or more additional therapeutic compound may occur separately. Alternatively, the compositions of the present invention and one or more additional therapeutic compound may be combined in one administration or delivery method, for example in one capsule, one caplet or one intravenous administration.

ACE Inhibitors

ACE inhibitors are compounds that inhibit the conversion of angiotensin I into angiotensin II by the enzyme angiotensin converting enzyme (ACE). Angiotensin II prevents blood vessels from relaxing and expanding thereby raising blood pressure. ACE inhibitors are used to treat high blood pressure, belong to the antihypertensive class of medicines and may reduce risk of death from cardiovascular disease by 20% to 40%. Inhibiting ACE allows blood vessels to relax and lowers blood pressure. ACE inhibitors lower arteriolar resistance and increase venous capacitance, increase cardiac output and cardiac index, stroke work and volume, lower renovascular resistance, and lead to increased natriuresis (excretion of sodium in the urine). Epidemiological and clinical studies have shown that ACE inhibitors reduce the progress of diabetic nephropathy independently from their blood pressure-lowering effect. This action of ACE inhibitors is utilized in the prevention of diabetic renal failure.

ACE inhibitors have been shown to be effective for indications other than hypertension even in-patients with normal blood pressure. The use of a maximum dose of ACE inhibitors in such patients (including for prevention of diabetic nephropathy, congestive heart failure, prophylaxis of cardiovascular events) is justified because it improves clinical outcomes, independent of the blood pressure lowering effect of ACE inhibitors.

Generally, ACE inhibitors are not prescribed for patients with kidney problems or with low blood pressure, although people with low blood pressure, surprisingly enough, often tolerate ACE inhibitors quite well. ACE inhibitors should not be used in pregnant women. Some ACE inhibitors are used to treat congestive heart failure or may be used for other conditions as determined by a physician.

ACE inhibitors may be classified based on the presence of functional groups on the compounds. For example, sulfhydryl containing compounds include captopril (CAPOTEN®, Bristol-Myers Squibb). Dicarboxylate containing compounds include enalapril (VASOTEC® by Merck), quinapril (ACCUPRIL® by Pfizer), lisinopril (PRINIVIL® by Merck or Zestril by Astra-Zeneca), perindopril (ACEON® by Rhone-Polenc Rorer), and ramipril (ALTACE® by Hoechst Marion Roussel, King Pharmaceuticals). Phosphate containing compounds include perindopril (ACEON® by Rhone-Polenc Rorer).

Other ACE inhibitors include benazepril (LOTENSIN® by Novartis), fosinopril (MONOPRIL® by Bristol-Myers Squibb), moexipril (UNIVASC® by Schwarz Pharma), trandolapril (MAVIK® by Knoll Pharmaceutical (BASF)) and the like. The ACE inhibitors can be classified into sulfhydryl, phosphate, and dicarboxylate compounds.

Of these compounds, several ACE inhibitors are commonly used as antihypertensive agents. These include benazepril, captopril, cilazapril, enalapril, enalaprilat, fosinopril, lisinopril, moexipril, perindopril, quinapril, ramipril, and trandolapril.

Several ACE inhibitors are commonly used as vasodilators, or for the treatment of congestive heart failure. These include benazepril, captopril, cilazapril, enalapril, fosinopril, lisinopril, quinapril, ramipril, and randolapril.

Lisinopril, captopril, ramipril, and trandolapril are used in some patients after a heart attack. After a heart attack, some of the heart muscle is damaged and weakened. The heart muscle may continue to weaken as time goes by. This makes it more difficult for the heart to pump blood. Lisinopril use may be started within 24 hours after a heart attack to increase survival rate. Captopril, ramipril, and trandolapril help slow down the further weakening of the heart.

Captopril is also used to treat kidney problems in some diabetic patients who use insulin to control their diabetes. Over time, these kidney problems may get worse. Captopril may help slow down the further worsening of kidney problems.

Ramipril is used together with an ACE inhibitor to treat vascular disease and related disorders, including but not limited to patients with coronary artery disease, congestive heart failure, hypertension and also diabetics with hypertension.

Other compounds not listed herein, but that have actions on reducing or inhibiting catalysis of angiotensin I to angiotensin II are also contemplated for use in the present invention.

In one embodiment, the amount of ACE inhibitor is between about 0.1 mg/day and about 100 mg/day. In other embodiments, ACE inhibitor is administered at a dose between about 1 mg/day and about 80 mg/day. In still other embodiments, ACE inhibitor is administered at a dose between about 5 mg/day and about 50 mg/day. A dose of ACE inhibitor may be administered at a starting dose of 5, 10, or 20 mg daily.

Alpha Lipoic Acid

Alpha-lipoic acid, also known as thioctic acid, is a disulfide compound that is a cofactor in vital energy-producing reactions in the body. It is also a potent biological antioxidant. Alpha-lipoic acid was once thought to be a vitamin for animals and humans. There are, however, certain situations, for example, diabetic polyneuropathy, where alpha-lipoic acid might be conditionally essential. Alpha-lipoic acid is found widely in plant and animal sources.

Most of the metabolic reactions in which alpha-lipoic acid participates occur in mitochondria. These include the oxidation of pyruvic acid (as pyruvate) by the pyruvate dehydrogenase enzyme complex and the oxidation of alpha-ketoglutarate by the alpha-ketoglutarate dehydrogenase enzyme complex. It is also a cofactor for the oxidation of branched-chain amino acids (leucine, isoleucine and valine) via the branched-chain alpha-keto acid dehydrogenase enzyme complex.

Alpha-lipoic acid is approved in Germany as a drug for the treatment of polyneuropathies, such as diabetic and alcoholic polyneuropathies, and liver disease. Alpha-lipoic acid contains a chiral center and consists of two enantiomers, the natural R- or D-enantiomer and the S- or L-enantiomer. Commercial preparations of alpha-lipoic acid consist of the racemic mixture, i.e. a 50/50 mixture of the R- and S-enantiomers.

Alpha-lipoic acid and its reduced metabolite, dihydrolipoic acid (DHLA), form a redox couple and may scavenge a wide range of reactive oxygen species. Both alpha-lipoic acid and DHLA can scavenge hydroxyl radicals, the nitric oxide radical, peroxynitrite, hydrogen peroxide and hypochlorite. Alpha-lipoic acid, but not DHLA, may scavenge singlet oxygen, and DHLA, but not alpha-lipoic acid, may scavenge superoxide and peroxyl reactive oxygen species.

Exogenous alpha-lipoic acid has been shown to increase ATP production and aortic blood flow during reoxygenation after hypoxia in a working heart model. It is thought that this is due to its role in the oxidation of pyruvate and alpha-ketoglutarate in the mitochondria, ultimately enhancing energy production. This activity, and possibly its antioxidant activity, may account for its possible benefit in diabetic polyneuropathy.

Most pharmacokinetic studies have been performed in animals. Alpha-lipoic acid is absorbed from the small intestine and distributed to the liver via the portal circulation and to various tissues in the body via the systemic circulation. The natural R-enantiomer is more readily absorbed than the S-enantiomer and is the more active form. Alpha-lipoic acid readily crosses the blood-brain barrier. It is found, after its distribution to the various body tissues, intracellularly, intra-mitochondrialy and extracellularly.

Dihydrolipoic Acid

Alpha-lipoic acid is metabolized to its reduced form, dihydrolipoic acid (DHLA), by mitochondrial lipoamide dehydrogenase. DHLA, together with lipoic acid, form a redox couple. It is also metabolized to lipoamide, which functions as the lipoic acid cofactor in the multienzyme complexes that catalyze the oxidative decarboxylations of pyruvate and alpha-ketoglutarate. Alpha-lipoic acid may be metabolized to dithiol octanoic acid, which can undergo catabolism.

To date, alpha-lipoic acid in doses up to 600 milligrams daily has been well tolerated. In some conditions such as diabetic neuropathy 300 milligrams of alpha-lipoic acid is administered daily, taken in divided doses.

Dihydrolipoic acid (DHLA) may also be used with the ACE inhibitor as described above for alpha lipoic acid.

In one embodiment of the present invention, the amount of lipoic acid or lipoic acid derivative administered is between about 1 mg/day and about 1000 mg/day. In other embodiments, lipoic acid or lipoic acid derivative is administered at a dose between about 10 mg/day and about 600 mg/day. In still other embodiments, lipoic acid or lipoic acid derivative is administered at a dose between about 100 mg/day and about 400 mg/day. A dose of lipoic acid or lipoic acid derivative is administered at a starting daily dose of 300 mg, 400 mg, 500 mg or 600 mg.

Statins

Another therapy which may be combined with the compositions of the present invention or a combination thereof, includes statins.

The statins (or HMG-CoA reductase inhibitors) form a class of hypolipidemic agents, used as pharmaceuticals to lower cholesterol levels in people with or at risk for cardiovascular disease. They cause cholesterol lowering by inhibiting the enzyme HMG-CoA reductase, an enzyme involved in the rate of cholesterol synthesis. Inhibition of this enzyme in the liver stimulates LDL-receptors, which results in an increased clearance of LDL from the bloodstream and a decrease in blood cholesterol levels. The first results can be seen after one week of use and the effect is maximal after four to six weeks.

Statins include Atorvastatin (LIPITOR®, TORVAST®); Fluvastatin (LESCOL®), Lovastatin (MEVACOR®, ALTOCOR®), Mevastatin, Pitavastatin (LIVALO®, PITAVA®), Pravastatin (PRAVACHOL®, SELEKTINE®, LIPOSTAT®), Rosuvastatin (CRESTOR®), and Simvastatin (ZOCOR®, LIPEX®).

In one embodiment, the amount of statin is between about 1 mg/day and about 100 mg/day. In other embodiments statin is administered at a dose between about 10 mg/day and about 80 mg/day. In still other embodiments, statin is administered at about 20 mg/day and about 60 mg/day.

Other Useful Therapeutic Agents

The pharmaceutical compositions of the present invention may also be administered together with one or more of the therapeutic substances disclosed in this paragraph. Anti-inflammatory drugs, for example aspirin, may be administered. The fatty acid reuptake inhibitor ezetimibe (Zetia® MSP Singapore Company, LLC, Whitehouse Station, N.J.) is also useful in the present compositions. Ezetimibe may also be combined with statins to produce combination drugs such as Vytorin® (MSP Singapore Company, LLC, Whitehouse Station, N.J.). Drugs to reduce the tendency of platelet aggregation, such as clopidogrel bisulfate, or clotting, such as heparin, may also be administered. Agents that have actions directly or indirectly on the cardiovascular system are included in this category, including but not limited to niacin, fibrates such as fenofibrate and gemfibrozil, and thiazolidinediones.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Synthesis of 3,4-methylenedioxyphenyl acetate, 3,4-methylenedioxy-6-nitrophenyl acetate and 3,4-methylenedioxy-6-nitrophenol Synthesis of 3,4-methylenedioxyphenyl Acetate (also called O-acetylmethylenedioxyphenol) [#2] from 3,4 methylenedioxyphenol (also called Sesamol) [#1].

In step I, an intermediate compound (3,4-Methylenedioxyphenyl acetate also called O-Acetylmethylenedioxyphenol and INV-73 herein) is made by the acetylation of 3,4 methylenedioxyphenol [#1].

In this example, acetylation was achieved using acetic anhydride. The acetylated product serves as the starting point of many other derivatives compositions, such as the nitro, amino, and carboxyl derivatives. While not wishing to be bound by theory, the inventors believe that the acetyl function may serve in an analogous capacity as the acetyl group in aspirin (acetyl salicylic acid) and may act to inhibit the aggregation of platelets.

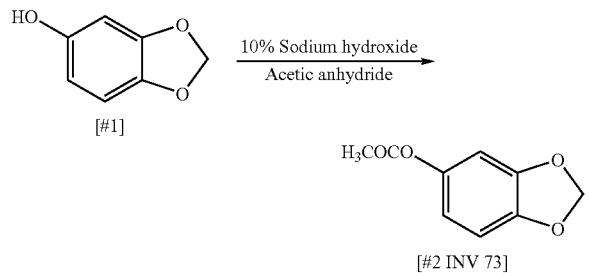

In Step II, the synthesis of 3,4-methylenedioxy-6-nitrophenyl acetate (also called O-acetyl nitromethylenedioxyphenol or INV-75 herein) from 3,4-Methylenedioxyphenyl Acetate [#2, INV-73] is achieved as follows:

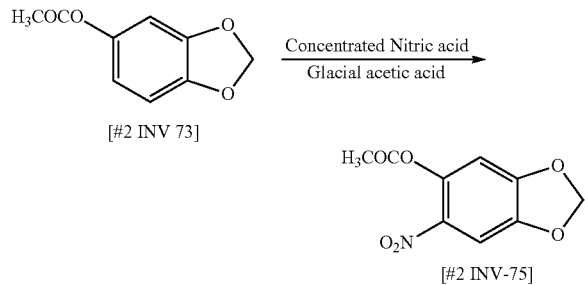

In Step III, the synthesis of 3,4-Methylenedioxy-6-nitrophenol (also called nitromethylenedioxyphenol and INV-74 herein) [#4] from 3,4-methylenedioxy-6-nitrophenyl acetate [#3, INV-75], is achieved as follows:

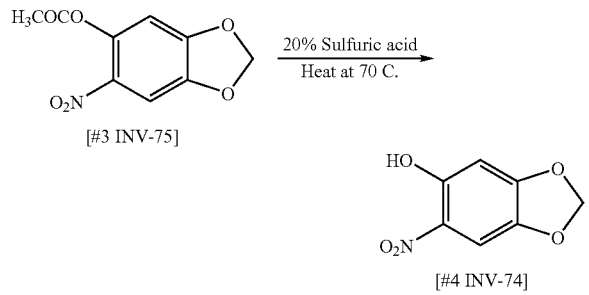

EXAMPLE 2

Biological testing of 3,4-methylenedioxy-6-nitrophenyl acetate (also called O-acetyl nitromethylenedioxyphenol or INV-75 herein): In Vitro Studies Cell Culture: All experiments were performed with cultured Human Umbilical Vein Endothelial Cells (HUVECs—Gibco, Invitrogen) and grown to confluence at 37° C. in a 5% $CO_2$ humidified incubator, on tissue culture flasks previously coated with 1% gelatin in supplemented culture medium (M199 with 10% heat inactivated fetal calf serum, 100 U/ml penicillin, 100 µg/ml streptomycin, 2 mM glutamine, 10 mM HEPES, pH 7.4, heparin 12 I.U./ml, 1% retinal derived growth factor, Sigma). Following trypsin treatment, the cells were detached from the flasks and final mono-layers were prepared by seeding HUVECs on gelatin-precoated culture plates and then incubated for 24-48 h to ensure confluence. Cells up to the fourth passage were used for all experiments. Recombinant human TNF-α was purchased from R&D Systems (Minneapolis, Minn.).

Cell Toxicity Assays: Cellular toxicity was assessed by MTT [3-(4,5-dimethylthiazol-2-yl)-2,5-diphenyltetrazolium bromide] assay, a commercially available assay for assessment of cellular viability. INV-75 was added to HUVECs for 24 hours, and toxicity assays were performed at the end of this period. The MTT assay relies on the cellular reduction of positively charged tetrazolium salts to their intensely colored formazan product by mitochondrial dehydrogenases. Formazan production is decreased in the presence of impaired mitochondrial redox function and enhanced free radical production and may, therefore, be used as an index of cell viability responses to experimental interventions.

Figure 2:
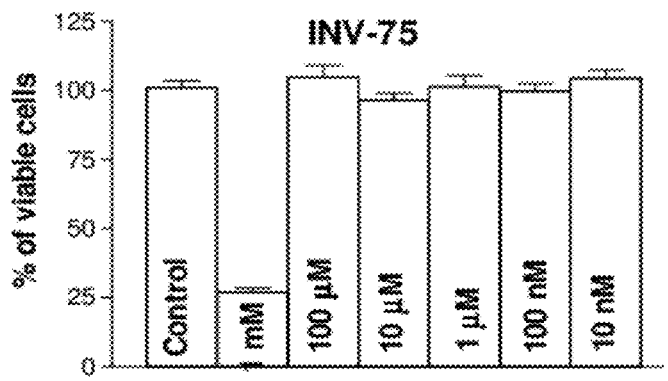
FIG. 2 is graph showing cell based toxicity assays for INV-75. Human umbilical vein endothelial cells were used in the experiments.

In short, after removing microtiter plates from the incubator, fresh medium containing a fixed volume of reconstituted MTT [3-(4,5-dimethylthiazol-2-yl)-2,5-diphenyltetrazlium bromide; final concentration: 0.5 mg/ml] was added to the wells; the plates were kept at 37° C. in a 5% $CO_2$ environment for 2 h, and then the MTT solubilization solution provided by the manufacturer was added. The formazan product formed by the conversion of positively charged tetrazolium salts to the reduced state has low aqueous solubility and is present as purple crystals. Dissolving the formazan with a solubilization buffer (provided in kit) permits the convenient quantification of its formation. Optical density at OD 570 nm is then measured for each well on an absorbance plate reader. The within- and between-assay variability was 3 and 5%, respectively. Various concentrations of INV-75 was tested in cell based assays using the MTT assay, as described above. The concentrations tested ranged from 1 mM to 10 nM and the cells were exposed for over 24 hours in duration (FIG. 2).

These results demonstrated that concentrations up to 100 mM resulted in 2%, 4%, 8%, and 7% cells displaying toxicity at 10 nM, 100 nM, 1 µM, 10 µM and 100 µM compared to 74% at 1 mM (p=0.001 for 1 mM compared to all other doses). These results were identical to that obtained for the other compounds INV-73, INV-74 and INV-7065. These results confirm the safety of INV-73, INV-74, INV-7065 across the dose range of 10 nM to 100 µM.

Enzyme-Linked Immunosorbent Assay (ELISA): To measure the expression of cell surface adhesion molecules, ELISA technique was utilized (R and D Systems, Minneapolis, Minn.). Confluent human umbilical HUVEC in 96-well plates were pretreated with INV-75 at various concentrations (1 mM, 10 µM, 1 µM, 100 nM and 1 nM for 24 hours before being stimulated with 2 ng/mL TNF-α for 6 hours.

Figure 3:
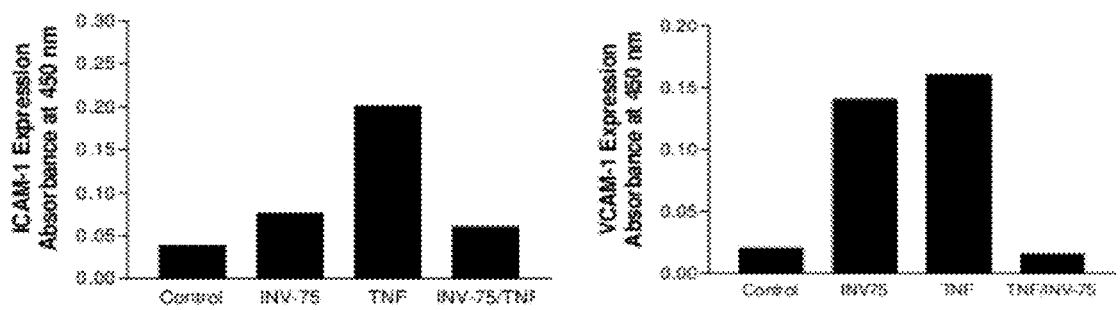
FIG. 3 demonstrates release of ICAM-1 and VCAM-1 in response to INV-75 AND TNF-α.

The results of ELISA analysis of culture media after one experiment with INV-75 pre-treatment are shown in FIG. 3 showed marked reduction in release of ICAM-1 and VCAM-1 (no statistics are shown). In subsequent experiments we also tested the effects of INV-75 on VCAM-1 expression by western blot. These results showed a reduction in VCAM-1 protein levels by pre-treatment of INV-75 but not with control (vehicle) alone treatment (see section and FIG. 24).

NF-κB Translocation Assays: Cytokines such as TNF-α and interleukin-1 (IL-1) activate a pro-inflammatory response in endothelial cells. An early event in this response is nuclear translocation of the NF-κB transcription factor.

This translocation causes the transcription of pro-inflammatory genes such as adhesion molecules VCAM-1, ICAM-1 and E-Selectin to be induced.

NF-κB is a heterodimer, composed of p65 and p50 subunits. Nuclear translocation is monitored by immunolocalization of the p65 subunit of NF-κB in fixed cells and is quantified by measuring the ratio of nuclear to cytoplasmic NF-κB signal. The nuclear translocation of NF-κB in stimulated cells such as primary human umbilical vein endothelial cells (HUVECs) therefore provides a readout that can be used to study the effects of bioactive compounds on the responsiveness of endothelium to pro-inflammatory stimuli. HUVECs were pre-treated with INV-75 at various concentrations (10 nM to 1 µM) or control (without [INV-75) for 24 hours. The media was then changed to one containing 10 ng/ml TNFα, or 1 µg/ml bovine serum albumin (vehicle) for 6 hours. p65 distribution was calculated as intensity in the cytoplasm and nucleus in regions of interest. At least 5 cells per high power field were used and at least 5 high power fields per concentration of the drug were used. The intensities were then expressed as the ratio of nuclear to cytoplasmic staining at least 5 cells per high power field. The data was then expressed as a ratio of the nuclear to cytoplasmic ratio without TNF-α.

In alternate experiments to assess NF-κB Activation extraction reagents were used to extract nuclear and cytoplasmic fraction from HUVEC cells previously treated with INV-75 at various concentrations for 6-24 hours before being stimulated with 2 ng/mL TNF-α for 6 hours. The expression of VCAM-1 and ICAM-1 were evaluated after TNF-α stimulation for 6 hours stimulation by western blot analysis. The p65 level in nuclear and cytoplasmic extracts were then analyzed by western blotting as described above. The effects of INV-75 on NF-κB translocation assays showed that INV-75 inhibits the translocation of p65 to the nucleus starting at 10 nM concentrations.

Figure 4:
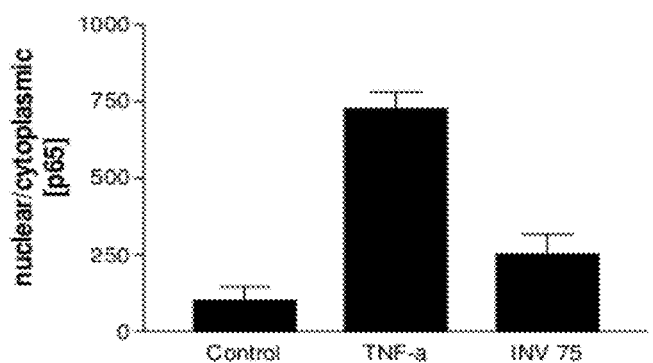
FIG. 4 is a graph showing the aggregate of multiple experiments assessing the effect of INV-75 on nuclear kappa factor kappa-B (NFkB). This is expressed as the nuclear to cytoplasmic ratios for p65, a sub-unit of NFkB for a control, TNF-α, and INV-75+TNF-α treated cells. A total of three experiments were performed. *, p<0.01 by ANOVA compared to vehicle.

The aggregate of multiple experiments with INV-75 is shown in FIG. 4. The nuclear to cytoplasmic ratio was compared between control cells treated with vehicle alone, in response to TNF-α and in response to TNF-α but after 24 hours of incubation with the drug. Pre-treatment with INV-75 resulted in a marked inhibition of nuclear p65 expression (n=3, p<0.01 by one-way ANOVA).

Sterol Regulatory Element Binding Protein (SREBP-2) Studies and Results:

A family of transcription factors designated SREBP (sterol regulatory element binding proteins) regulate synthesis of cholesterol and fatty acids. Of these, SREBP-2 mainly regulates cholesterol biosynthesis by alteration of cholesterol synthesis enzymes and LDL receptor expression (SREBP-1c mainly regulates fatty acid synthesis). SREBP-2 is predominantly regulated through post-transcriptional mechanisms and is processed in the Golgi apparatus to a mature form after trafficking from the endoplasmic reticulum. To study the effect of INV-75 on SREBP, the following in vitro experiments were performed: HepG2 (Human liver carcinoma cell line) cells were stimulated with INV-75 (0.1 mM) for four hours and corresponding SREBP2 nuclear binding by electrophoretic migration shift assay (EMSA) was assayed. The time course with this dose and dose dependence was analyzed. Next we assessed the expression of both precursor and mature form of SREBP-2 in the cytoplasm by western analysis. Both time course and dose dependence of mature form of SREBP-2 was analyzed.

Figure 5A:
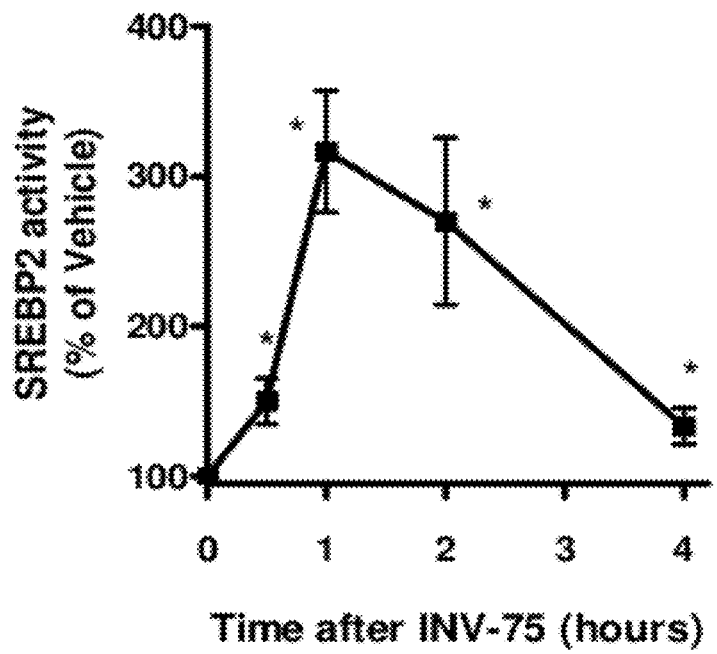
FIG. 5A is a graph showing in vitro time course of course of Sterol Regulatory and Binding Protein-2 (SREBP2) activity measurement with INV-75. HepG2 cells were stimulated with INV-75 (0.1 mM) for four hours and the binding activity of SREBP2 to nuclear proteins was measured by electrophoretic migration shift assay (EMSA). A total of three experiments were performed. *, p<0.01 by ANOVA compared to vehicle.
Figure 5B:
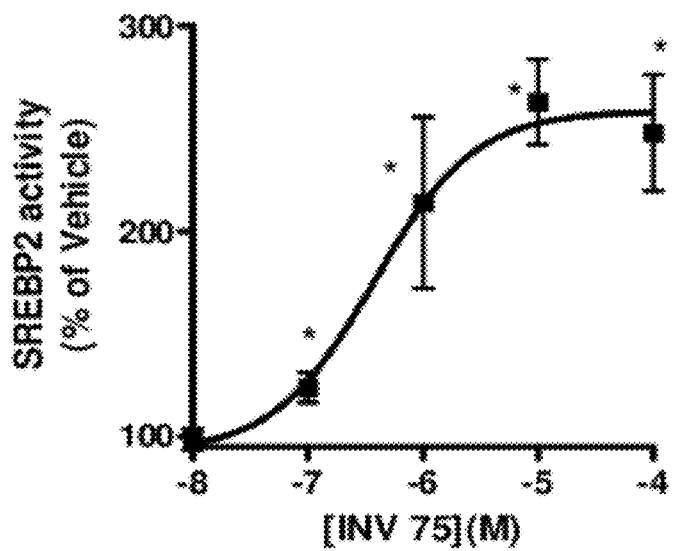
FIG. 5B is a graph showing the dose dependent effects of INV-75 on SREBP2 activity. HepG2 cells were stimulated with multiple concentrations of INV-75 for 1 hour and binding activity of SREBP2 in nuclear proteins was measured by electrophoretic migration shift assay (EMSA). A total of three experiments were performed. *, p<0.01 by ANOVA compared to vehicle.

FIGS. 5A and 5B depict the effect of INV-75 on nuclear binding of SREBP-2. INV-75 increased the nuclear binding of SREBP-2 in <1 hour after treatment (FIG. 5A). Doses as low as 100 nM were effective in inducing the translocation of SREBP-2 to the nucleus. FIG. 5B provides the aggregate of two such experiments.

Figure 5C:
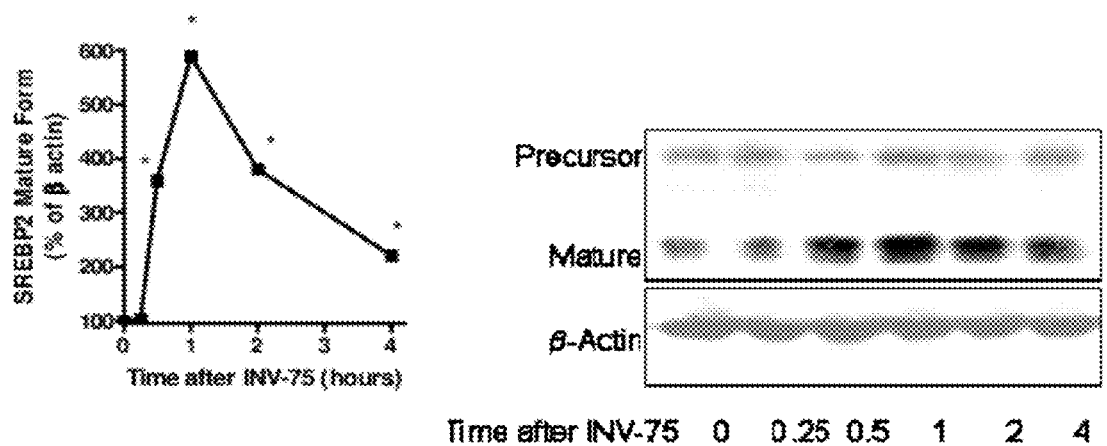
FIG. 5C is a graph showing in vitro time course SREBP2 activation measured by the assessment of the mature form with INV-75 in the cytoplasm of treated cells. HepG2 cells were stimulated with INV-75 (0.1 mM) for four hours and the mature and precursor forms of SREBP2 was measured by western blot analysis. A total of three experiments were performed. *, p<0.01 by ANOVA compared to vehicle. The corresponding western blot is depicted on the right. Time is in hours on the right.
Figure 5D:
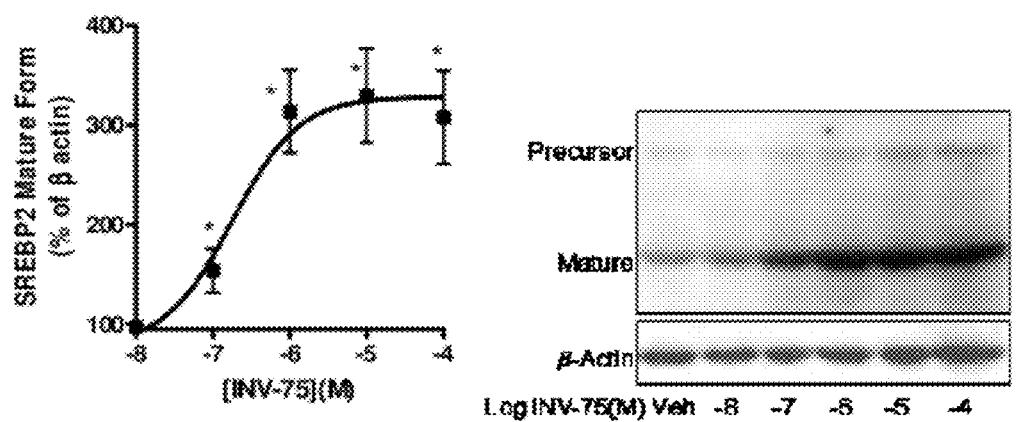
FIG. 5D is a graph showing dose dependent effects of INV-75 on SREBP2 activation assessed with mature form INV-75. HepG2 cells were stimulated with multiple concentrations of INV-75 for 1 hour and the mature and precursor forms of SREBP2 was measured by western blot analysis. A total of three experiments were performed. *, p<0.01 by ANOVA compared to vehicle. Dose of INV-75 is log molar concentration.

FIG. 5C and FIG. 5D provide the time course of INV-75 on the processing of SREBP-2 in the cytoplasm. These data suggest that INV-75 rapidly increase the processing of SREBP-2 from the precursor (immature form) to the mature form in a dose dependent fashion with doses as low as 10 nM having an effect in increasing the mature form of SREBP-2.

Figure 5E:
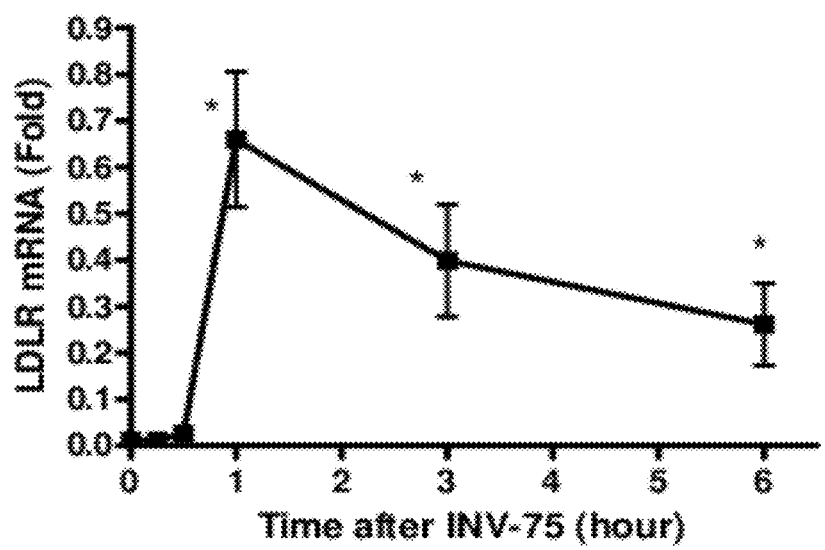
FIG. 5E is graph showing time course of low density lipoprotein receptor (LDLR) messenger RNA (mRNA) with INV-75 assessed by quantitative real time polymerase chain reaction (RT-PCR). A total of three experiments were performed. *, p<0.01 by ANOVA compared to vehicle.
Figure 5F:
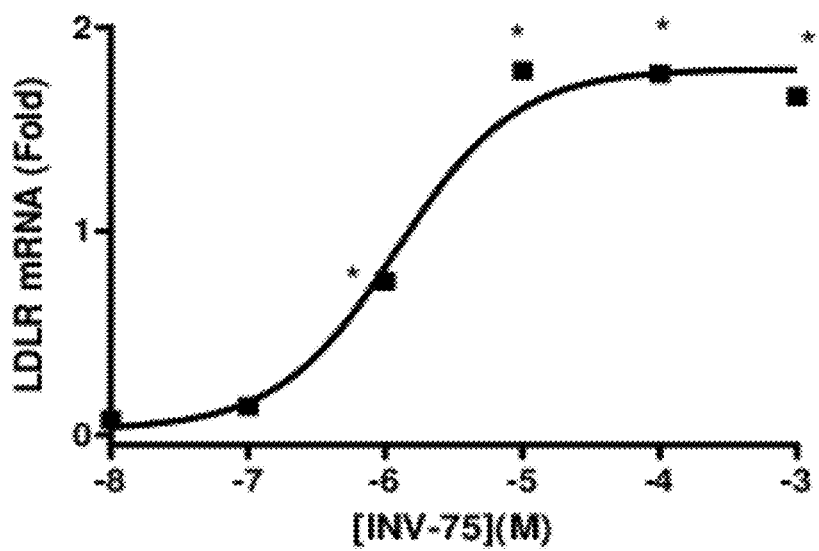
FIG. 5F is a graph showing dose dependency experiments of low density lipoprotein receptor (LDLR) messenger RNA (mRNA) measurement with INV-75. HepG2 cells were stimulated with multiple concentrations of INV-75 for 1 hour and LDL mRNA expression was measured by quantitative real time polymerase chain reaction (RT-PCR). A total of three experiments were performed. *, p<0.01 by ANOVA compared to vehicle. Dose of INV-75 is log molar concentration.

Next we investigated the effect of INV-75 in regulating LDL receptor expression in the same cells using a similar protocol to assess dose and temporal dependence. FIGS. 5E and 5F depict the time course of LDL receptor expression and dose dependence in response to INV-75. These results clearly show that INV-75 increases LDL receptor expression in a time dependent and dose dependent fashion. Taken together these results suggest that INV-75 may increase LDL receptor expression through an SREBP-2 dependent pathway. INV-75 had no effects on SREBP-1 regulation (data not shown). Simultaneously multiple genes involved in cholesterol synthesis and regulation, apolipoprotein gene expression and expression of PCSK9 (Proprotein convertase subtilisin/kexin type 9) was tested. The latter gene is known to regulate LDL receptor expression by binding to the epidermal growth factor-like repeat A (EGF-A) domain of the low-density lipoprotein receptor (LDLR), inducing LDLR degradation. Inhibition of PSCK9 function is currently being explored as a means of lowering cholesterol levels. The results revealed no effects of INV-75 on PCSK9 expression.

PPAR Activation Assays and Results

Figures 6A, 6B, 6C:
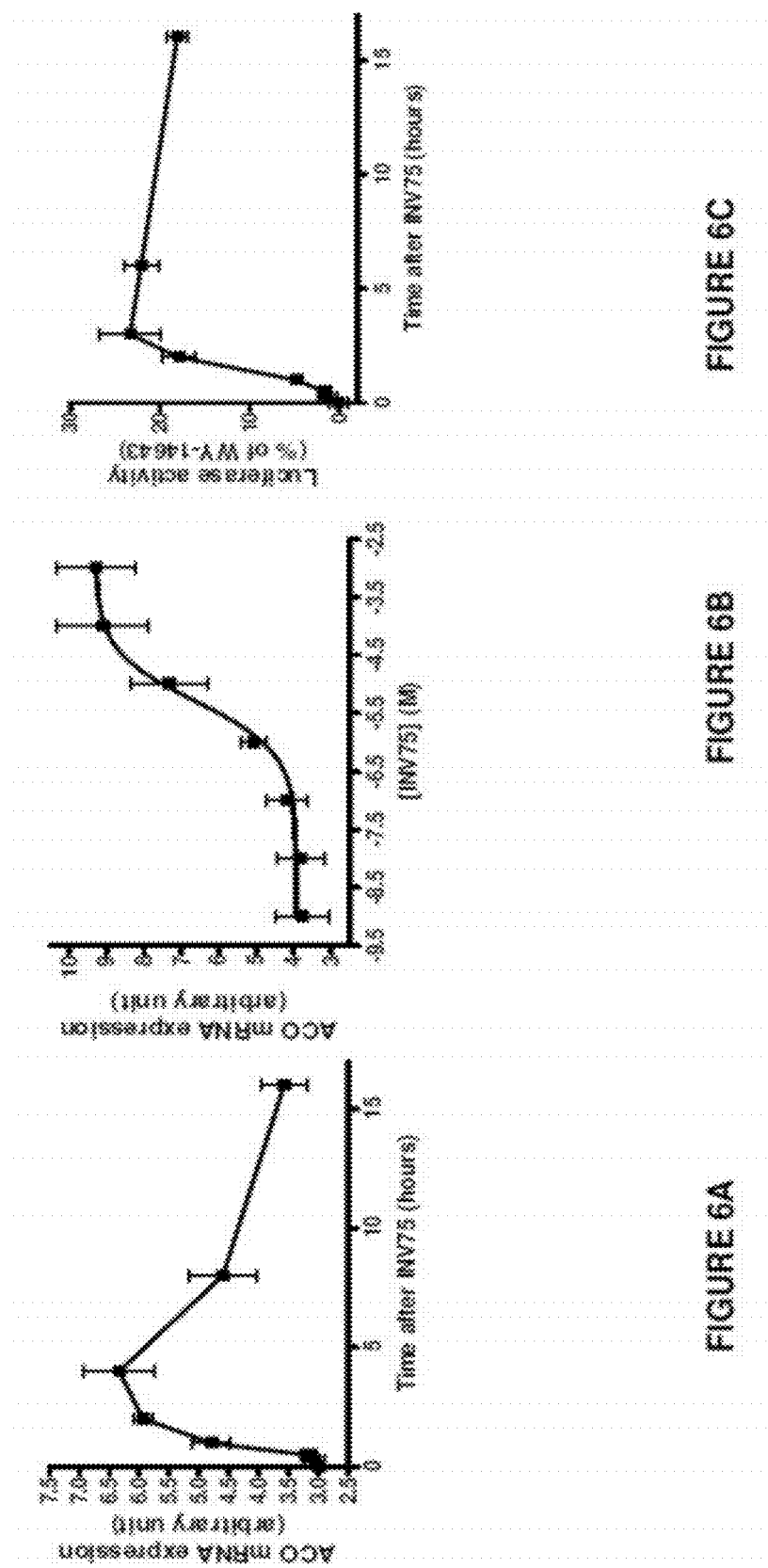
FIG. 6A shows the in vitro assessment of Peroxisome Proliferation Activator Receptor-alpha (PPARα) by INV-75 using acetyl-CoA Oxidase (ACO) as a surrogate. ACO is a PPAR-α regulated gene. HepG2 cells were stimulated by INV 75 (100 µM) for the indicated time, the mRNA expression level of ACO was analyzed by real-time RT-PCR. n=3. *, p<0.05 vs 0.
FIG. 6B shows the in vitro activation of ACO by INV-75 using HepG2 cells transfected by full length human PPARα linked to luciferase reporter. Cells were stimulated with INV-75 for 4 hours, and mRNA expression level of acetyl co-enzyme A oxidase (ACO) analyzed by real-time RT-PCR. n=3. *, p<0.05 vs −8.5.
FIG. 6C shows the time course experiment of PPARα gene activation by INV-75 expressed in relation to the activation by a high potency specific PPARα activator, WY 14643. HepG2 cells were transfected with the full length PPARα promoter reporter construct and stimulated by INV-75 (100 M). Results in C are expressed as % increase compared to WY 14643.

We used a reporter gene assay in HepG2 cells to screen for agonists of the peroxisome proliferator-activated receptors. Peroxisome proliferator-activated receptors (PPARs) and other members of the nuclear hormone receptor family are important drug targets for the treatment of metabolic diseases. PPARs play crucial roles in lipid and glucose metabolism, respectively. Therefore, screening methods that help to rapidly identify activators of these receptors should be of considerable value. INV-75 activated a classic PPARα gene, Acetyl-CoA Oxidase (ACO) in a dose dependent and time dependent fashion (FIG. 6A). The time course experiment was performed in presence of INV-75 up to 15 hours. Next we transfected cells with a human full length PPARα promoter-reporter construct and demonstrated that INV-75 increased luciferase activation (FIG. 6B). In the next experiment we addressed the time course of PPARα activation and demonstrated activation at times <1 hour and persistent effects on PPARα activation up to 15 hours (FIG. 6C). We next tested the specificity of INV-75 for PPARα by performing experiments in HepG2 cells transfected with yeast GAL4-PPARα-LBD plasmid+UAS-Luciferase; GAL4-PPARδ-LBD plasmid+UAS-Luciferase and GAL4-PPARα-LBD plasmid+UAS-Luciferase. The PPARα, PPARδ and PPARγ binding assays were performed using multiple concentrations of INV-75 (1 µM, 10 µM, 100 µM and 1000 µM). The level of luciferase activity corresponded to the degree of PPAR activation. The results were compared with classic PPAR agonists such as WY-14643 (PPARα agonist), Bezafibrate (PPARδ agonist) and Rosiglitazone (PPARα agonist). These results showed that INV-75 increased PPARα ligand binding activity in a selective fashion without effects on PPARα or PPARγ. Thus INV-75 has selective but partial agonist properties on PPARα activation.

EXAMPLE 3

Biological testing of
3,4-methylenedioxy-6-nitrophenyl acetate (also
called O-acetyl nitromethylenedioxyphenol or
INV-75 herein): In Vivo Studies In vivo experiments on hypercholesterolemic rabbits (Watanabe Heritable Hyperlipidemic Rabbits, WHHL) were performed in 6 rabbits treated with INV-75. Four rabbits served as controls.

Animal Model: WHHL rabbits weighing approximately 2 kg at 2 months were purchased from Brown Family in Alabama and housed in the institutional Laboratory Animal Center. Rabbits at the age of 6 months were used for all experiments. Rabbits were allowed free access to water and were fed a high cholesterol chow (2% cholesterol) from Harlan Tekad TD 7251. The animal care and experimental protocols were in accordance with nationally approved guidelines. The protocol that the rabbits were subjected to is outlined in FIG. 7. INV-75 was dissolved in 90% ethanol and sprayed on the high fat chow. The diet-drug mixture was then vacuum dried overnight to remove ethanol and then used to feed rabbits.

Figure 7:
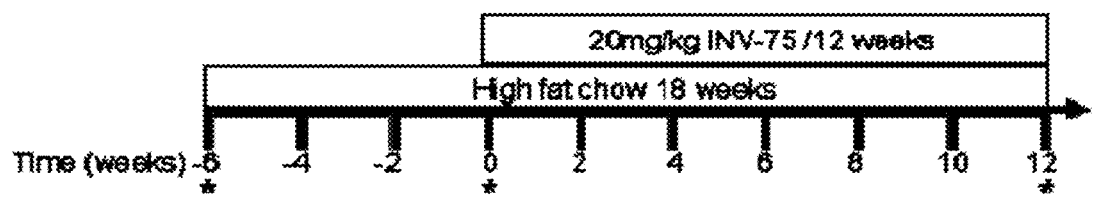
FIG. 7 is a schematic illustration of the in vivo WHHL rabbit experimental protocol using INV-75. The * represents the timing for MRI evaluation for imaging of plaque.

In Vivo Protocol (Rabbits):

Each animal underwent three MRI studies: the first one prior to high fat feeding (baseline prior to drug administration); the second at the mid-point of drug therapy; and the final study after 12 weeks of drug therapy (FIG. 7). The WHHL rabbits were allowed to adjust to their new environment after arrival following which baseline MRI measurements and blood work was obtained prior to high cholesterol chow feeding. Drug therapy with INV-75 was begun 4-6 weeks after high fat diet feeding. Mid point measurements were obtained during drug therapy. At the end of the study, all animals underwent an MRI study for plaque volume quantification. Immediately after the last MRI, the rabbits were euthanized and the aorta was harvested and processed for further analysis (histopathology, gene and protein expression. The study protocol was approved by an institutional animal research committee. Anesthesia for the interventions (MRI studies) was induced by intramuscular injection of ketamine (30 mg/kg) and xylazine (2.2 mg/kg). Approximately 5 cm of abdominal aorta above the celiac trunk was excised with sterile tools, washed in autoclaved phosphate buffered saline (PBS), and immediately frozen in liquid nitrogen and stored at −80° C. until processed for gene and protein expression. All animals received humane care in compliance with the "Guide for the Care and Use of Laboratory Animals."

Noninvasive MRI Protocol and Results

High-resolution non-invasive MRI served to assess the degree of atherosclerosis before and after the corresponding treatments. Atherosclerotic plaque in the abdominal aorta of WHHL rabbits was analyzed by in vivo MRI scans at the indicated time points (FIG. 7). This experimental design allows for each animal to serve as its own control, allowing for true serial data on plaque progression/regression as well as allowing comparison between treatment-groups. MRI studies were performed by using a 1.5-T magnet (Magnetom Sonata, Siemens Medical Solutions, Erlangen, Germany) using a phased array cardiac coil that was wrapped around the animal. Gradient-echo coronal and sagittal images were used to localize the abdominal aorta, and sequential transverse images (3-mm thickness segments with no gap) of the abdominal aorta were obtained from above the celiac trunk to the iliac bifurcation using a TURBO Flash sequence. Forty-eight 4 mm-thick axial slices spanning approximately from the iliac bifurcation to the superior pole of the topmost kidney were obtained using a T1-weighted gradient echo turbo FLASH protocol (TR/TE 230/5.0, 3 averages, slice thickness of 4.0 mm with a 5.2 mm gap between slices and a time of acquisition of about 11 minutes). No respiratory or cardiac gating was necessary as the abdominal aorta is relatively free from motion artifact. Plaque burden was determined by manually tracing the external elastic lamina (EEM) and the luminal border (L) and determining the area within each boundary using Siemens Viewer software. Slice volume (V) was calculated as V=(EEM-L)*4.0 and total wall volume per animal was calculated using the formula TWV= $\Sigma[(EEM-L)*4]$ and expressed in mm$^3$. TWVs for each animal at each time point were normalized for varying numbers of readable slices with the formula NWV=(TWV/n)*m; n=number of slices readable in the individual animal and m=mean number of slices readable in all animals over all time points. All normalized wall volumes were reported in mm$^3$. The wall volume in the rabbit abdominal aorta, an indication of atherosclerotic plaque, was analyzed by serial in vivo MRI scanning. After 4-6 weeks of feeding with high cholesterol chow, WHHL rabbits had larger abdominal aorta wall volume than age-matched normal chow-fed New Zealand rabbits did, supporting that atherosclerosis was established.

Figure 8A:
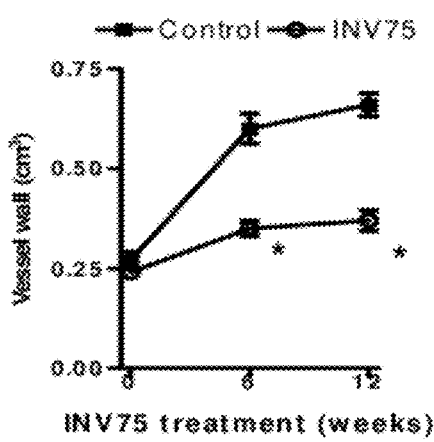
FIG. 8A illustrates and assessment of atherosclerotic plaque burden determined by MRI at three different point (baseline, 6 weeks and 12 weeks).

FIG. 8A depicts the effects of treatment with INV-75 on progression of plaque as assessed by MRI. The MRI measurements were performed at baseline (after initiation of HFC, but before the initiation of INV-75, at mid point during drug treatment and shortly before sacrifice. The MRI studies were transferred on to a PC for analysis and plaque volumes analyzed using Image J software. The images were matched for anatomic position by using distances from the renal arteries and iliac bifurcation so that true serial data on atherosclerotic changes could be obtained. The aortas immediately distal to the celiac trunk were selected for vessel wall measurements. All MRI images were acquired and analyzed blinded to the study arm or the histopathology data. Mean (SEM) normalized wall volumes (NWVs) in the control and INV-75 groups at baseline, prior to supplementation with INV-75, were 0.27 cm$^3$ (0.021 cm$^3$) and 0.24 cm$^3$ (0.0099 cm$^3$), respectively. These were not significantly different (p=0.2775 by one-way ANOVA).

Figure 8B:
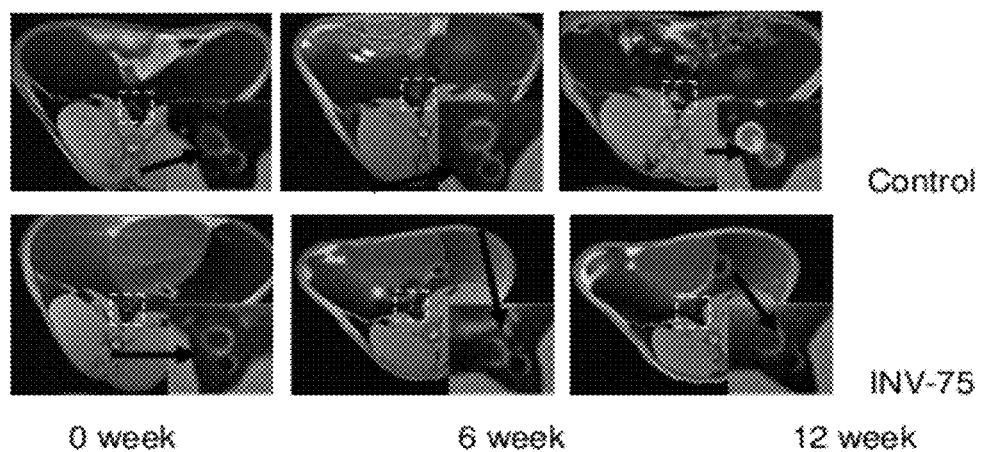
FIG. 8B is a collection of representative MRI images indicating a decrease in atherosclerosis burden in the abdominal aorta in INV-75 treated WHHL rabbit compared to control WHHL rabbit.

After 6 weeks of dietary supplementation with INV-75, wall volume in the abdominal aorta was significantly reduced compared to the control arm. At the study midpoint, following treatment with INV-75, mean (SEM) plaque volumes in the control and INV-75 groups were 0.60 cm$^3$ (0.037 cm$^3$) and 0.35 cm$^3$ (0.019 cm$^3$), respectively. These were significantly different (p=10.0004 by one-way ANOVA). At the end of 12 weeks, there was a more pronounced slowing of the rate of progression of plaque in the group that received treatment with INV-75 with wall volumes (SEM) in the control and INV-75 groups being 0.66 cm$^3$ (0.029 cm$^3$) and 0.37 cm$^3$ (0.025 cm$^3$), respectively at 12 weeks. These were significantly different (p=0.0001 by one-way ANOVA). The earlier time point of 6 weeks was also statistically significant compared to control treatment. FIG. 8B depicts representative MRI images of abdominal aortic plaque in animal subjected to control or INV-75 at various time points.

Morphometric Analysis to Assess anti-atherosclerotic effects of INV-75

Figure 9:
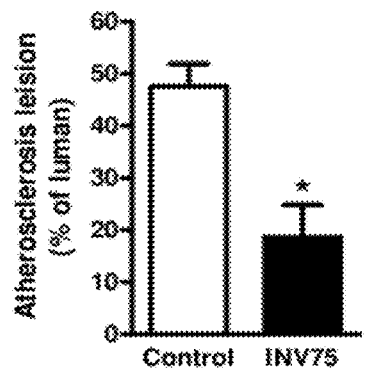
FIG. 9 is a bar diagram representation of atherosclerotic burden in abdominal aorta of control and INV-75 groups of WHHL rabbits are presented. n=5/group. *, p<0.05 vs control animals by unpaired t test. About 60% reduction in atherosclerosis burden in WHHL rabbits compared to WHHL group receiving control intervention. All animals were fed a high fat chow.

Segments of descending thoracic aorta were embedded in Optimal Cutting Temperature compound (Tissue-Tek, Sakura Finetek USA Inc, Torrance, Calif.) and frozen on dry ice. En face sections were then prepared. To analyze atherosclerotic burden, 8 sections (4 μm thick) were collected at intervals of 20 μm. After H&E staining, each section was digitized with a digital camera and analyzed using a microscope (Zeiss Axioskop with Spot I digital camera, Jena, Germany) with National Institutes of Health (NIH) Image software version 1.61. Results were expressed as mm². Morphometric assessment of plaque burden in the thoracic aorta at the end of 12 weeks corroborated the anti-atherosclerotic effects of INV-75 by MRI on the abdominal aorta. The summary of atherosclerotic burden in abdominal aorta of control and INV-75 groups of WHHL rabbits are presented. n=5/group. *, p<0.05 vs control animals, n=4, using un-paired t test. Approximately 60% reduction in atherosclerosis burden in WHHL rabbits compared to control group was observed (FIG. 9).

Figure 10:
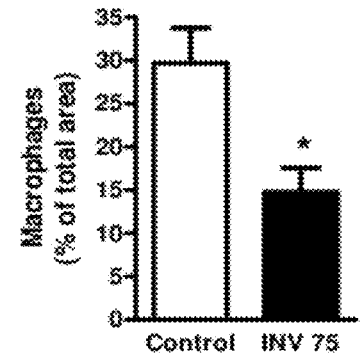
FIG. 10 is a morphometric analysis of macrophage infiltration in the thoracic aorta of Watanabe Heritable Hyperlipidemic Rabbit (WHHL) in INV-75 treated animals, *p<0.05, vs. controls by unpaired t test. All animals were fed a high fat chow.
Figure 11:
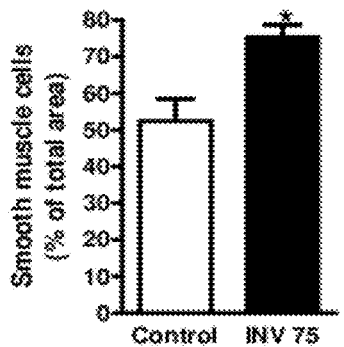
FIG. 11 is a morphometric analysis of smooth muscle cell (SMC) proliferation in aortic wall by anti-α-actin stain on control and INV-75 treated WHHL animals, *p<0.05 vs. controls by unpaired t test. All animals were fed a high fat chow.

Immunohistochemistry Approach and Results:

Immunohistochemical staining was performed to assess inflammatory content using the primary antibodies (1:200 concentration) and a detection system (Immunoperoxidase Secondary Detection System; Chemicon International, Temecula, Calif.), and quantified with software (NIH Image) after digitization of the images with a camera system (Zeiss Axioskop with Spot I digital camera). Antibodies against CD68 were purchased from Santa Cruz Biotechnology Incorporated (Santa Cruz, Calif.). A polyclonal anti-α-Actin antibody was obtained from Upstate Cell Signaling Solutions (Lake Placid, N.Y.). T cell receptor β antibody was obtained from Biolegend (San Diego, Calif.). To quantify the staining, the mean density of 4 negative control (no primary antibody) sections was set as the threshold, and positive area was acquired by software. Results were finally normalized by the area subtended by the external elastic lamina to the luminal interface or the intimal-medial volume. The effects of INV-75 on macrophages and smooth muscle cells in comparison to control group were evaluated by CD68 and α-actin immunohistochemistry, respectively. INV-75 decreased the number of macrophages vs. controls and summary of whole groups is represented by bar diagram in FIG. 10 (n=4-5 animals/group). *p<0.05 vs control animals using unpaired t test). INV-75 treated group showed significant inhibition of macrophage infiltration as illustrated in FIG. 10. INV-75 increased the smooth muscle content (% of total area) vs controls and the combined results were represented as a bar diagram n=5/group (n=number of animals used per group). *p<0.05 vs control animals.

p<0.05 represents three or more matched values are Gaussian and values are within the statistical limit. Immunohistochemical analysis of thoracic aortic sections revealed a reduction in CD68$^+$ cells in atherosclerotic plaque but increased smooth muscle proliferation (FIG. 10 and FIG. 11).

Figure 12:
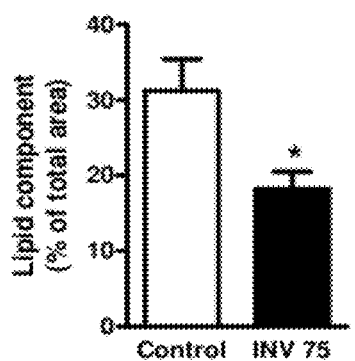
FIG. 12 is a morphometric analysis of lipid deposition in aortic wall by Red oil O stain on control and INV-75 treated WHHL animals, *p<0.05, One way ANOVA. All animals were fed a high fat chow.
Figure 13:
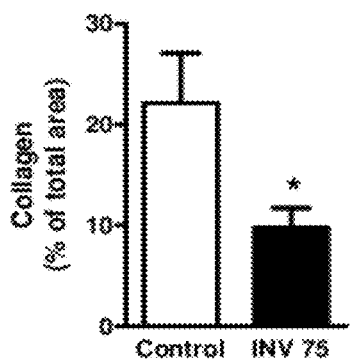
FIG. 13 is a morphometric analysis of collagen deposition in aortic wall by Masson trichrome stain on control and INV-75 treated WHHL animals, *p<0.05, One way ANOVA. All animals were fed a high fat chow.

Lipid deposition in aorta was identified after total 14 weeks of treatment with drug, rabbits were sacrificed and abdominal aortas were fixed in 4% paraformaldehyde. The lipid deposition in aortic wall was then visualized by oil red staining. Oil Red O staining of the abdominal aorta showed a reduction in lipid content in the plaque area calculated as percentage of threshold area of abdominal aortic sections of INV-75 treated animals compared to control group. INV-75 decreased lipid component significantly vs controls (FIG. 12). Masson's trichrome staining of abdominal aorta showed reduction in collagen content in the plaque area calculated as percentage of threshold area of abdominal aortic sections of INV-75 treated animals compared to control group. (FIG. 13).

Lipid profile: TC, TG, HDL, LDL and VLDL

Hypercholesterolemia and oxidative stress occupy an important function in the progress of atherosclerosis. Lipids (cholesterol and LDL) in the blood were evaluated by analyzing the blood samples both at the baseline and the end point measurements. 1 ml of blood from an ear lobe vein was placed into K EDTA tubes at a start of high cholesterol diet and again at the time of sacrifice. All values were expressed as mean±SD. The bar graph of each group for total cholesterol and LDL cholesterol at baseline prior to the initiation of high fat chow, following high fat chow but before intervention and at the end of intervention with INV-75 and control are presented. (FIG. 14A and FIG. 14B). There were no differences at the end of treatment with INV-75 in total cholesterol or in LDL cholesterol. The lack of effect may relate to the genetic model (WHHL) which has extremely high lipid values and a mutation in the LDL receptor. Since INV 75 is believed to function by increasing LDL clearance through an increase in LDL receptor expression, the lack of effect on LDL cholesterol and total cholesterol (major lipoprotein fraction in this model at baseline and in response to high fat chow feeding) is understandable.

Endothelial function: Organ Chamber Experiments to Study Vascular Physiological Effects Rabbits were euthanized by injection of lethal doses of pentobarbital. The ascending aortas was removed and 2 mm thoracic aortic rings were suspended in individual organ chambers filled with physiological salt solution buffer (sodium chloride, 130 mEq/L; potassium chloride, 4.7 mEq/L; calcium dichloride, 1.6 mEq/L; magnesium sulfate, 1.17 mEq/L; potassium diphosphate, 1.18 mEq/L; sodium bicarbonate, 14.9 mEq/L; EDTA, 0.026 mEq/L; and glucose, 99.1 mg/dL [5.5 mmol/L]; pH, 7.4), aerated continuously with 5% carbon dioxide in oxygen at 37° C. Vessels were allowed to equilibrate for at least 1 hour at a resting tension of 30 mN before being subjected to graded doses of agonists as described previously. The vasoconstrictor agonists included phenylephrine (PE), endothelin-1 (ET-1), or angiotensin II. Responses were expressed as a percentage of the peak response to 120 mEq/L of potassium chloride. The vessels subjected to PE were washed thoroughly and allowed to equilibrate for 1 hour before beginning experiments with acetylcholine, sodium nitroprusside (SNP) or insulin. After a stable contraction plateau was reached with PE (0.1 µM), the rings were exposed to graded doses of the endothelium-dependent agonist acetylcholine, insulin or the endothelium-independent agonist SNP. Results were expressed as a percentage of pre-contraction by PE (0.1 µM). The rings exposed to acetylcholine were thoroughly washed and allowed to equilibrate for 1 hour. After a stable contraction plateau was reached with PE (0.1 µM), insulin was then added in a cumulative manner followed by a wash and dose response to SNP. Results were expressed as a percentage of pre-contraction by PE (0.1 µM). INV-75 decreased aortic contraction by angiotensin II but had no effect on phenylephrine (FIG. 15 and FIG. 16).

In contrast to significant effects on responses to angiotensin II, INV-75 had no effects on response to PE, endothelin-1. INV 75 had significant effect on acetylcholine dependent vasodilation and marginal (non-significant effect on insulin (FIG. 17 and FIG. 18). INV-75 had no effects on SNP, an endothelium-independent vasodilator (results not shown). The decreased response to angiotensin II in INV-75 rabbits was paralleled by decreased mRNA expression of the angiotensin II Type I receptor (data not shown). Table 1 illustrates the summary of responses to various agonists in the thoracic aorta of WHHL rabbits.

TABLE 1

| | PE | | ET-1 | | AII | | Ach | | SNP | | Insulin | |
|---|---|---|---|---|---|---|---|---|---|---|---|---|
| | Max z | log EC50 | Max | log EC50 | Max | log EC50 | Max | log EC50 | Max | log EC50 | Max | log EC50 |
| CON | 132 ± 7 | 6.6 ± 0.1 | 52 ± 10 | 7.3 ± 0.3 | 20 ± 1 | 8.1 ± 0.1 | 27 ± 4 | 5.7 ± 0.2 | 81 ± 7 | 6.6 ± 0.2 | 69.3 ± 10.7 | 3.7 ± 1.2 |
| INV-75 | 135 ± 5 | 6.7 ± 0.1 | 47 ± 9 | 7.5 ± 0.4 | 13 ± 1* | 8 ± 0.2 | 74 ± 2*** | 6.3 ± 0.1* | 72 ± 6 | 6.8 ± 0.1 | 71 ± 9.9 | 4.2 ± 0.7 |

*p < 0.01;
***p < 0.001

Oxidative Stress Measures: 8-epi Prostaglandin F2α (8-Isoprostane) Enzyme Linked Immunoassay Plasma and liver samples were obtained from WHHL rabbits at the time of sacrifice. Liver lysates were prepared by homogenization in PBS. Both samples underwent affinity purification (Cayman Chemical, Ann Arbor, Mich.) and then measurement of 8-isoprostane with the Stat-8-Isoprostane ELISA kit (Cayman Chemical, Ann Arbor, Mich.). The levels in the liver were adjusted for protein. The protein levels in liver lysates were determined by BCA Protein Assay (Pierce, Rockford, Ill.).

8-epi Prostaglandin F2α (8-Isoprostane) production in plasma and aortic homogenates were significantly lower in the INV-75 groups compared to the control groups (FIG. 19, FIG. 20).

Detection of superoxide ($O_2^{\cdot-}$) by Dihydroethidium Staining

In situ detection of $O_2^{\cdot-}$ was performed in snap-frozen aortic tissues embedded in OCT compound (Tissue-Tek®, Sakura Finetek USA Inc, Torrance, Calif.). Tissue samples were cryosectioned at 20 μm of thickness, collected onto Superfrost Plus slides (Fisher Scientific, Pittsburg, Pa.), and stored at −80° C. until needed. Four slides that were randomly chosen from each rat (tissue block) were placed into phosphate buffered saline (PBS) for 30 min at room temperature and then stained with dihydroethidium (DHE, 10 μM, Molecular Probes, Inc., Eugene, Oreg.) in PBS for 20 min in a moist chamber in the dark. The slides were rinsed extensively with PBS, coverslipped, and digitally imaged with a microscope (Zeiss Axioskop with a Spot I digital camera, Jena, Germany). DHE is freely permeable to cells and in the presence of $O_2^{\cdot-}$, can undergo a two-electron oxidation to form the DNA-binding fluorophore ethidium bromide that is trapped intracellularly by intercalation into DNA. The reaction was relatively specific for $O_2^{\cdot-}$, with minimal oxidation induced by cellular peroxidases and hydrogen peroxide. For inhibitor studies, slides were incubated with 300 μM apocynin (Sigma), 10 μM diphenyliodonium (DPI, Fisher Scientific), or PEG-SOD (250 U/ml) for 30 min before being stained with DHE. The summary of results of whole group represented by bar diagram, *, p<0.01, represents three or more matched values are Gaussian and values are within the statistical limit.

The results revealed reduction in basal super oxide production in the aorta with INV-75 treated group (FIG. 21).

Lucigenin chemiluminescence for NADPH Derived Superoxide ($O_2^{\cdot-}$) detection: Effect of INV-75

Oxidative stress has been implicated in atherosclerosis. Superoxide ($O_2^{\cdot-}$) derived from NADPH could potentially trigger a free radical chain reaction which could potentially catalyze atherosclerotic plaque formation. Rabbit aorta was homogenized in PBS, and the protein concentration was adjusted to 5 μg/μl. 20 ul/well of cell lysates were plated on a 96-well microplate in Kreps-Hepes Buffer (pH=7.4; initially gassed with 95% $O_2$, and 5% $CO_2$). The baseline $O_2^{\cdot-}$ production was measured with 5 μM Lucigenin. NADPH induced $O_2^{\cdot-}$ production was measured by adding NADPH (100 μM). Measurements were performed with Berthold Luminometer LB 960. Luminometer settings were 0.1 s measurement and 30s kinetics.

Basal and stimulated superoxide production in aortic tissue lysates was found to be lower compare to normal control and statistical analysis was done based on n=5/group. *, p<0.05 vs. control animals for superoxide production (FIG. 22).

Inflammatory Gene and Protein Expression in Response to INV-75 and Controls

As vascular inflammation plays a pivotal role in atherosclerosis, assessment of pro-inflammatory gene expression and protein expression provides additional information on the anti-inflammatory effects of INV-75.

Quantitative RT-PCR Analysis

Total RNA was isolated with TRIzol reagent (Invitrogen). Four microgram of total RNA was reverse transcribed by random hexamers and ThermoScript RT-PCR System (Invitrogen). Quantitative real-time PCR was performed with the Stratagene Mx3005 using SYBER Green PCR Master Mix (Applied Biosystems, Foster City, Calif.). Relative expression level compared to GAPDH was obtained. The primers used in the experiment are depicted in the table below and were purchased from Invitrogen.

TABLE 2

| Gene | Sense/Antisense | Seq ID No. | Sequence |
|---|---|---|---|
| Rabbit ICAM-1 | Sense | 1 | 5'-GCC TGA GGT CCA GTT CTG TG-3' |
| | Antisense | 2 | 5'-GCG GAC ACA GCT CTC AGT AG-3' |
| Rabbit GAPDH | Sense | 3 | 5'-GCC TGG AGA AAG CTG CTA AG-3' |
| | Antisense | 4 | 5'-CCA GCA TCG AAG GTA GAG GA-3' |
| Rabbit VCAM-1 | Sense | 5 | 5'-TGC CGA GCT AAA TTA CAT ATC G-3' |
| | Antisense | 6 | 5'-TCA TTG TCA CAG AGC CAC CT-3' |
| Rabbit P-selectin | Sense | 7 | 5'-CGG ACC AGA AAG ACT GGA CT-3' |
| | Antisense | 8 | 5'-GTT CCT CAC ATG GTG CTG GAC-3' |

TABLE 2-continued

| Gene | Sense/Antisense | Seq ID No. | Sequence |
|---|---|---|---|
| Rabbit L-selectin | Sense | 9 | 5'-GCT CAG AAG GAG CCG AGT TA-3' |
| | Antisense | 10 | 5'-TTA CCA TGA CTG CCA CAG GA-3' |
| Rabbit MCP-1 | Sense | 11 | 5'-AGC ACC AAG TGT CCC AAA GA-3' |
| | Antisense | 12 | 5'-TGT GTT CTT GGG TTG TGG AA-3' |

Western Blot Analysis

Samples were homogenized and solubilized in radioimmunoprecipitation assay buffer (50 mM Tris-HCl, pH 7.4, 150 mM NaCl, 1 mM EDTA, 1 mM NaF, 1 mM $Na_3VO_4$) and 1 mM phenylmethylsulfonyl fluoride, with 0.25% sodiumdeoxycholate and 1.0% Nonidet P-40) and centrifuged at 10,000 g and 4° C. for 30 min. The supernatant was collected and subjected to Western blot analysis. In brief, 40 μg of protein was separated by SDS-polyacrylamide gel electrophoresis and subsequently transferred to nitrocellulose membrane. The membrane was then incubated with: monoclonal anti-β-actin (Sigma, St. Louis, Mo.), monoclonal anti-VCAM (R&D Systems, Minneapolis, Minn.), monoclonal anti-ICAM (R&D Systems, Minneapolis, Minn.), monoclonal anti-phospho-eNOS(pS 1177) (BD Biosciences, Billerica, Mass.), rabbit anti-eNOS (Santa Cruz Biotechnology, Santa Cruz, Calif.), rabbit anti-phospho-Akt (Thr308) (Cell Signaling Technology, Danvers, Mass.), goat anti-Akt (Santa Cruz Biotechnology, Santa Cruz, Calif.), and rabbit anti-p65 (Cell Signaling Technology, Danvers, Mass.). Finally, the membranes were incubated with a horseradish peroxidase-linked secondary antibody and visualized with an enhanced chemiluminescence kit (Amersham Biosciences Inc., Piscataway, N.J.). Band density was quantified by densitometric analysis using ImageJ.

INV-75 decreased mRNA expression of VCAM-1, ICAM-1, MCP-1, and L-selectin in thoracic aorta (FIG. 23). We corroborated the effect of INV 75 on VCAM-1 and ICAM gene expression in aorta by measuring expression of these adhesion molecules at the protein level. FIG. 24 depicts the summary of western blot analysis for VCAM-1 and ICAM-1 expression. INV-75 markedly reduced the protein expression of VCAM-1 and ICAM-1.

We have also examined the effects of INV-75 in cell culture to understand its effects on regulation of the adhesion molecule VCAM-1. We had previously shown that iNV-75 reduced NF-kB activation and expression of VCAM-1 and ICAM-1 in HUVEC cells (see FIG. 3 and FIG. 4). We reconfirmed these findings but additionally asked the question if these results may relate the activation of PPARα as previously demonstrated in FIG. 6, where we showed that INV-75 activates PPARα receptor and PPARα regulated genes such as ACO. HUVECs were pretreated with vehicle, INV-75, or WY-14643 for 2 hours, and then treated with TNFα for 4 hours. VCAM-1 expression was analyzed at the end of this duration. A representative and summary of three independent experiments are presented. *, $p<0.05$ vs control; #, $p<0.05$ vs TNFα (FIG. 25). These experiments suggest that VCAM-1 decrease seen with INV-75 may perhaps relate to its effects on PPARα activation.

Sterol Regulatory Element Binding Protein (SREBP-2) Activity: in vivo Experiment Since we had previously shown effects of INV-75 in regulating SREBP-2 and LDL receptor in cell culture we proceeded to confirm these results in vivo in a mouse model (C57Bl/6 mice). To study the effect of INV-75 on SREBP activity in vivo experiment was performed as follows: C57bl/6 mice (6/group) were intraperitoneally injected with INV-75 (20 mg/kg/day, for two weeks). The binding activity of SREBP2 in nuclear proteins of liver homogenates was measured by electrophoretic migration shift assay (EMSA). Simultaneously multiple genes involved in cholesterol synthesis and regulation, apolipoprotein gene expression and expression of PCSK9 (Proprotein convertase subtilisin/kexin type 9) were also studied in the liver. PCSK9 is known to regulate LDL receptor expression by binding to the epidermal growth factor-like repeat A (EGF-A) domain of the low-density lipoprotein receptor (LDLR), inducing LDLR degradation.

Results demonstrated that INV-75 significantly lowered LDL but not other lipoproteins (FIG. 27). This is paralleled by an increase in LDL receptor expression in liver as measured by real-time RT-PCR (FIG. 26) and western blot-(data not shown). INV-75 also dramatically activated SREBP2, the critical transcription factor regulating LDLR, as measured by electrophoretic migration shift assay (EMSA) (FIG. 28).

These results confirm that INV-75 can up-regulate LDLR through activation of SREBP2 thereby decreasing LDL cholesterol levels. The results further strengthen our findings that INV-75 has pronounced beneficial effect on the lowering of LDL.

EXAMPLE 4

Synthesis of 3,4-Methylenedioxyphenyl lipoate (O-Lipoyl methylenedioxyphenol) from methylenedioxyphenol and dl-lipoic acid (INV-7065)

The compound 3,4-Methylenedioxy phenyl lipoate ($C_{15}H_{18}O_4S_2$) (also called O-lipoylmethylenedioxyphenol and INV-7065 herein) has a molecular weight (MW) of 326.43 and has a formula of $C_{15}H_{18}O_4S_2$. INV 70-65 was made by the treatment of lipoic acid and methylenedioxyphenol using halogenated solvent under nitrogen atmosphere.

In a 250 mL round bottom flask, 4.5 g (0.033 mole) of 3,4-methylenedioxyphenol (Aldrich, catalog # S3003-25G-A) and 5 g (0.4 mole) of dimethylamino pyridine (Aldrich, catalog #522821) and 120 mL of dichloromethane were stirred well for 15 minutes at room temperature. 7.4g (0.036 mole) of alpha lipoic acid (Geronova Research Inc) was added by portions over a period of 10 minutes. N-(3-Dimethylaminopropyl)-N'-ethylcarbodiimide hydrochloride (EDCI Aldrich, catalog #: E7750) 8.6 g (0.8 mole) was added over a period of 45 minutes and continued to stir over night. All solvents are commercial grade and purchased from Fisher Scientific. It is to be understood that other halogenated solvents may be used, including but not limited to chloroform and carbon tetrachloride. It is to be understood that other coupling agents may be used, including but not limited to dicyclocarbodiimide (DCC) and diisopropylcarbodiimide (DIC).

After about 24 hours of reaction time, thin layer chromatography (3:1 hexane: ethyl acetate solvent system) of the crude product was checked with the starting materials to check the formation of product and disappearance of the starting material 3,4-methylenedioxyphenol. After complete reaction, the dichloromethane was evaporated under reduced pressure. A thick yellow mass obtained which was directly purified using flash column chromatography with a 3:1 hexane: ethyl acetate solvent system. Slow elution of solvent from column chromatograph is necessary to obtain the product in higher purity. A yellow fluffy solid obtained was re-purified by a crystallization method. The crystallization was performed using 90% ethanol and the procedure involves slow addition of the compound INV-7065 (about 2 g) over a period of 10 minutes into a warm ethanol (about 35 mL) with continuous stirring. After complete dissolution of the compound, a pale yellow solution was filtered quickly and placed aside for slow crystallization overnight. A shining fluffy solid was filtered and dried using a vacuum dryer. The total yield was 65% -73%. The crystallized product was characterized using high resolution proton NMR. The following is a schematic representation of the reaction:

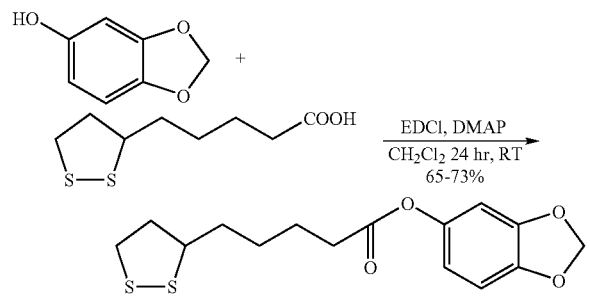

Figure 1A:
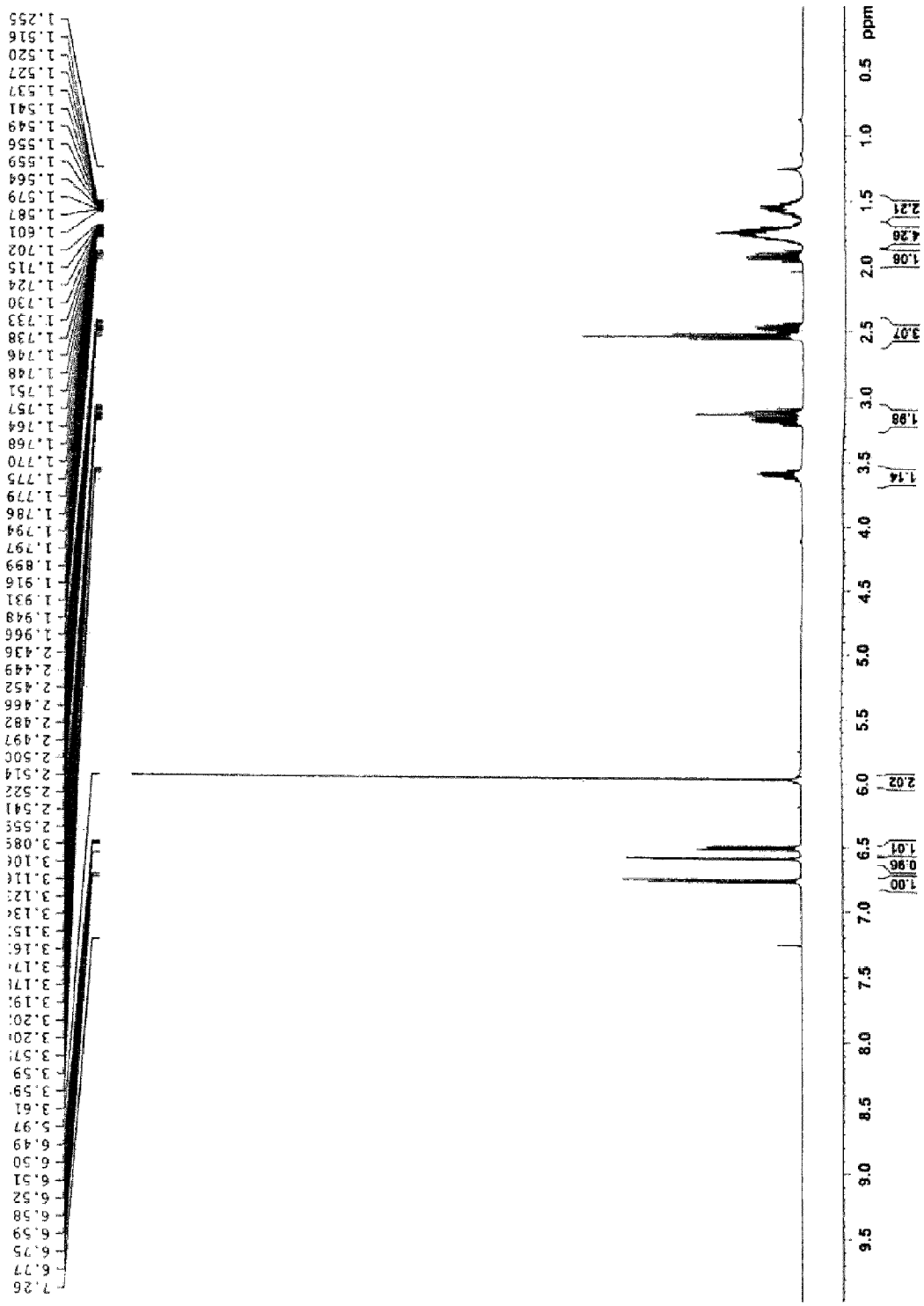
FIG. 1A shows the proton NMR of INV-7065.
Figure 1B:
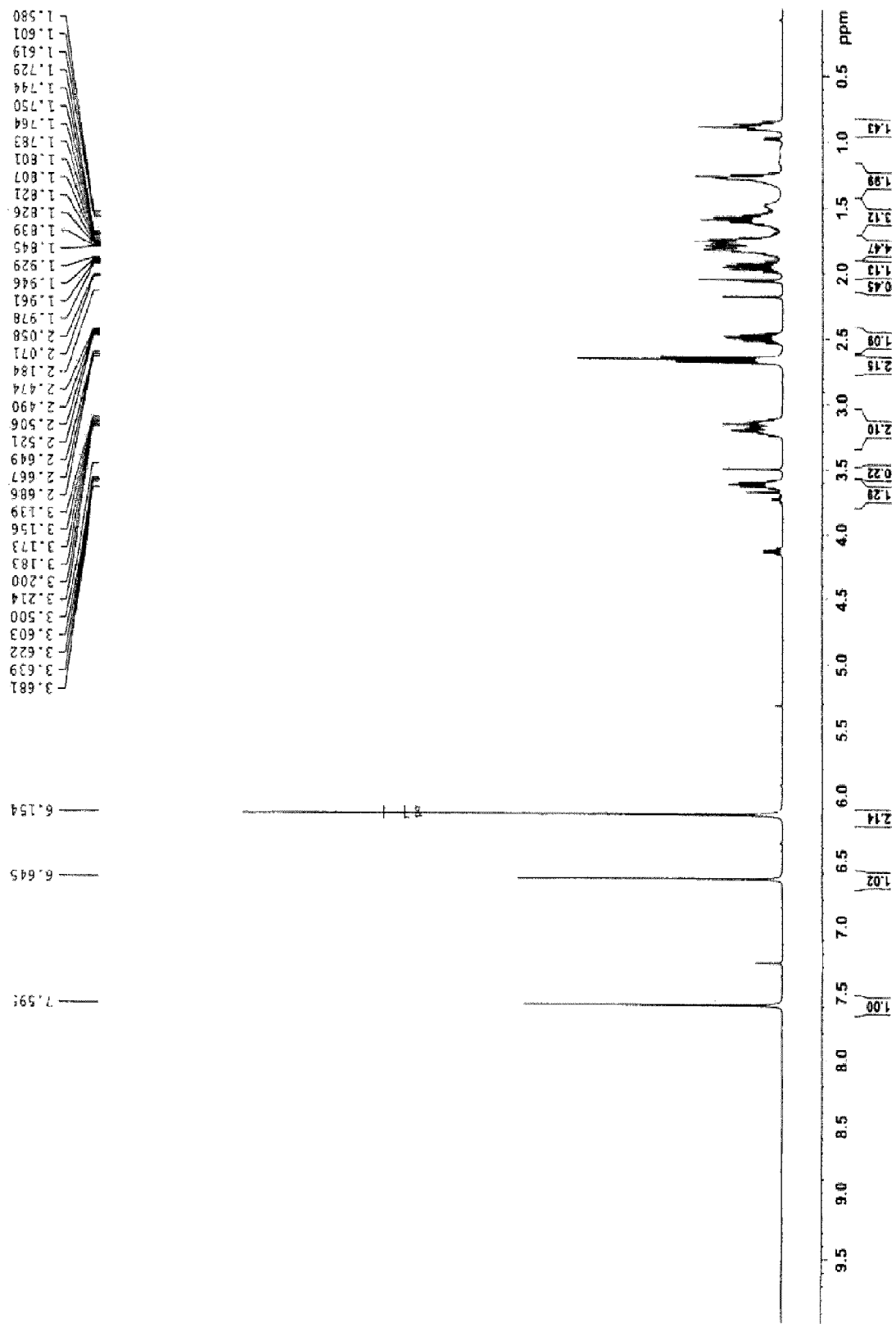
FIG. 1B shows the proton NMR of INV-7465.

NMR characterization: The crystallized compound was characterized by high resolution proton NMR and the typical proton chemical shift values of the product are ($CDCl_3$): 6.77-6.75 (1H, doublet), 6.59-6.58 (1H, doublet), 6.52-6.49 (1H, doublet of doublet), 5.97 (2H, singlet), 3.61-3.57 (1H, multiplet), 3.19-3.10 (2H, multiplet), 2.56-2.52 (2H, triplet), 2.51-2.45 (2H, multiplet), 1.95-1.86 (2H, multiplet), 1.79-1.73 (4H, multiplet), 1.58-1.53 (2H, multiplet). FIG. 1B.

EXAMPLE 5

Biological Activity of 3,4-Methylenedioxyphenyl lipoate (INV 70-65)

Since INV 70-65 was made by the treatment of lipoic acid and methylenedioxyphenol, we attempted to understand its effects especially in comparison to that of lipoic acid alone to help distinguish effects of lipoic acid versus that of methylenedioxyphenol. Thus in our experiments involving in vivo testing one of the comparator groups was lipoic acid.

Animal Model: 15 male New Zealand White rabbits (Charles River, Mass.) were fed with high fat diet (HFD) (Harlan Teklad rabbit diet with 0.5% cholesterol, TD 87251). After 4 weeks of high fat diet, rabbits were randomized into three different treatment groups, normal control (n=5), lipoic acid (100 mg/kg/day) (n=5), INV 70-65 (100 mg/kg/day) (n=5). These drugs were administered to the animals via their chow by mixing the drugs with the high fat diet. A fixed amount of chow and drugs admixed in the chow were fed to all animals every day after carefully calculating food intake in each rabbit. Drugs were dissolved in 100% ethanol and sprayed onto the diet and kept under vacuum to let ethanol evaporate overnight. Two (2) weeks after drug or control admixed HFD, all rabbits underwent aortic balloon denudation surgeries followed by 12 weeks of continued administration of drug or controls admixed with HFD. FIG. 29 provides an outline of the experimental design.

Magnetic Resonance Imaging Protocol for Assessment of Atherosclerosis

MRI experiments were conducted at two time points: 1 week and 12 weeks after the balloon denudation procedure (FIG. 29). Preceding MRI acquisitions, rabbits were anesthetized with an intramuscular injection of xylazine (2 mg/kg) and ketamine (40 mg/kg) and an i.v. catheter (Surflo 24G× ¾", TERUMO® Medical Corp., Elkton, Md.) was placed in a marginal ear vein for the later administration of contrast. Pre and post MRI images to assess atherosclerosis using a double inversion T1-weighted gradient echo turbo FLASH sequence were obtained using a 1.5 T 32-channel whole body MR system (MAGNETOM Avanto, Siemens, Germany). For imaging, rabbits were placed in a prone position and were wrapped in a flexible 6-element phase array body coil. Thirty 4 mm-thick transversal slices (4.6 mm gap between slices), perpendicular to the descending aorta spanning approximately from the iliac bifurcation to the superior pole of the topmost kidney, were acquired with: TR/TE=260/5 ms, 312× 312 µm in-plane resolution, bandwidth 120 kHz, three signal averages and a total scan time of 12 minutes, 29 seconds. Following the pre-contrast acquisition, 7-10 ml solution of 0.1 mmol/Kg Magnevist (Bayer HealthCare Pharmaceuticals Inc. Wayne, N.J.) was injected through the catheter and flushed with 2 ml of saline. A repeat of the pre-contrast dark blood scan was started approximately 6 min and 30 seconds post contrast administration. After the post-contrast scan, rabbits were allowed to recover. MR images were analyzed using a Siemens Leonardo Workstation (Siemens Healthcare Inc. Germany).

To assess the different rates of atherosclerosis plaque progression for each rabbit group, the aortic wall was identified in the pre-contrast images at both MRI time points. Regions of interest (ROI) were free hand drawn around the inner and outer vessel wall border in 10 to 22 images for each animal. Vessel wall area was obtained in each slice by subtracting the lumen area from the area encapsulated by the outer border of the vessel wall. A total vessel wall volume for each animal was obtained by multiplying the slice thickness (4.6 mm) times the total vessel wall area (in mm). To account for the variable number of slices, for each rabbit a normalized aortic wall volume was calculated.

To assess plaque neovasculature progression in the different treatment groups, only the 12 weeks post balloon denudation MR images were used. Identical ROIs encapsulating the aortic wall were hand drawn in 7 to 11 pre and post-contrast MRI images. The signal to noise ratio (SNR) for each slice was calculated as the mean signal obtained from the vessel wall divided by the standard deviation of the noise from a region outside the body. A ratio of the SNR enhancement for each rabbit was obtained by dividing the post and pre contrast calculated SNRs.

FIG. 30A depicts MRI assessment of plaque burden in the various groups. INV 70-65 resulted in marked attenuation of plaque burden following 12 weeks of treatment compared to control animals. There was no difference between lipoic acid treatment and INV 70-65 treatment in this experiment. Control animals fed HFD continued to increase the atherosclerotic plaque burden.

FIG. 30B depicts the contrast enhancement of the aorta following gadolinium administration in the various treatment groups. FIG. 30B depicts a reduction in gadolinium enhancement following INV 70-65 treatment compared to controls and lipoic acid treatment.

Vascular Function: Myograph Experiments to Study Vascular Physiological Effects of INV 70-65 in Comparison with Control and Lipoic Acid Treatment Rabbits were euthanized by injection of lethal doses of pentobarbital. The thoracic aortas were collected for the myograph studies. Two (2) mm thoracic aortic rings were suspended in individual organ chambers filled with physiological salt solution buffer (sodium chloride, 130 mEq/L; potassium chloride, 4.7 mEq/L; calcium dichloride, 1.6 mEq/L; magnesium sulfate, 1.17 mEq/L; potassium diphosphate, 1.18 mEq/L; sodium bicarbonate, 14.9 mEq/L; EDTA, 0.026 mEq/L; and glucose, 99.1 mg/dL [5.5 mmol/L]; pH, 7.4), aerated continuously with 5% carbon dioxide in oxygen at 37° C. Vessels were allowed to equilibrate for at least 1 hour at a resting tension of 30 mN before being subjected to graded doses of agonists. The vasoconstrictor agonist phenylephrine (PE) was used and responses were expressed as a percentage of the peak response to 120 mEq/L of potassium chloride. The vessels subjected to PE were washed thoroughly and allowed to equilibrate for 1 hour before beginning experiments with acetylcholine or sodium nitroprusside (SNP). After a stable contraction plateau was reached with PE (0.1 μM), the rings were exposed to graded doses of the vasodilators that included the endothelium-dependent agonist acetylcholine and insulin or the endothelium-independent agonist SNP. Results for the vasodilators were expressed as a percentage of pre-contraction by PE (0.1 μM). Table 3 summarizes the vascular responses, while FIGS. 31A-31D depict the results.

We observed about 80% reduction in lipid deposition in the aortic wall of INV-7065 treated animals compared to controls and about 40% reduction when compared to lipoic acid.

Plasma Lipid Profile Study

A lipid profile (Cholesterol, Triglycerides, direct HDL, LDL and VLDL) was performed after a total of 12 weeks of treatment with the drugs. One (1) ml of blood from the ear lobe vein was placed into tubes containing K EDTA at the beginning of the high cholesterol diet and again at the time of sacrifice. All values were expressed as mean±SD. The bar graph of each group both at the baseline and the end point measurement is presented. The statistical analysis was done with one way ANOVA. There were moderate decreases in TC and LDL level at the end of treatment with INV-75 and lipoic acid group compared to normal control, FIG. 32A and FIG. 32D.

On the other hand, triglyceride (TG) levels significantly decreased in INV-7065 and lipoic acid groups compared to controls, FIG. 32B. HDL levels in the lipoic acid group increased moderately while INV-7065 showed an insignificant change, FIG. 32C. INV-7065 treated animals showed a slight decrease in VLDL whereas lipoic acid treated animals showed no change in VLDL levels compare to controls FIG. 32E. These results suggest that INV-7065 is moderately effective in controlling lipid profiles compare to controls and lipoic acid treated animals.

TABLE 3

Summary of vascular responses in thoracic aorta at the end of 12 weeks of INV 70-65

| | Control | | Lipoic Acid | | 3,4-Methylenedioxy phenyl lipoate (INV-7065) | |
|---|---|---|---|---|---|---|
| | LogEC50 (M) | Maximum Effect (%) | LogEC50 (M) | Maximum Effect (%) | LogEC50 (M) | Maximum Effect (%) |
| Ach | −5.99 ± 0.33 | −12.27 ± 2.54 | −6.47 ± 0.18 | −33.00 ± 2.94* | −6.67 ± 0.16 | −29.84 ± 2.09* |
| PE | −6.65 ± 0.08 | 159.4 ± 6.12 | −6.48 ± 0.09 | 154.0 ± 7.24 | −6.28 ± 0.08 | 109.1 ± 4.78† |
| SNP-1 | −6.83 ± 0.19 | −84.36 ± 6.24 | −6.75 ± 0.21 | −89.04 ± 7.67 | −7.09 ± 0.16 | −83.06 ± 4.95 |
| Insulin | 1.72 ± 0.12 | −114.7 ± 14.53 | 1.39 ± 0.09 | −107.8 ± 7.68 | 1.47 ± 0.139 | −132.5 ± 14.59† |

† = p < 0.05 versus lipoic acid;
*p < 0.05 versus control

FIG. 31A and FIG. 31B depict a differential effect of INV 70-65 on responses to phenylephrine and insulin. INV 70-65 improved relaxation to peak doses of Insulin compared to lipoic acid but had no effect on EC50 doses.

In contrast, INV 70-65 was no different than lipoic acid in improving response to acetylcholine when compared to control (FIG. 31C). In contrast, there were no differences in any of groups in response to the endothelium independent agonist sodium nitroprusside (SNP). These results suggest that INV 70-65 decreases vascular contractility to alpha receptor agonist and increases vascular insulin sensitivity.

Immunohistochemistry Approach and Results

Hypercholesterolemia and oxidative stress play an important role in the development of atherosclerosis. The rabbits were sacrificed and abdominal aortas were fixed in 4% PFA (paraformaldehyde). The lipid deposition in the aortic wall was then visualized by oil red staining. Oil Red O staining of the abdominal aortas showed a reduction in lipid content in the plaque area calculated as percentage of threshold area of abdominal aortic sections of 3,4-Methylenedioxy phenyl lipoate and lipoic acid treated animals compared to the control group. *, p<0.05, One way ANOVA.

EXAMPLE 6

Synthesis and purification of 3,4-Methylenedioxy 6-nitro phenyl lipoate (O-Lipoyl nitromethylenedioxyphenol) (INV-7465)

3,4-Methylenedioxy 6-nitro phenyl lipoate has a molecular weight of 371.43 and a formula of $C_{15}H_{17}NO_6S_2$. 3,4-Methylenedioxy 6-nitro phenyl lipoate is also called O-Lipoyl nitromethylenedioxyphenol and INV-7465 herein.

Synthesis and purification methods of 3,4-Methylenedioxy 6-nitro phenyl lipoate Method-I The synthesis of 3,4-Methylenedioxy 6-nitro phenyl lipoate was achieved by reaction between nitromethylenedioxyphenol (3,4-methylenedioxy 6-nitrophenol) and alpha lipoic acid and is schematically represented below. The synthesis of nitromethylenedioxyphenol (INV-74) was described earlier in this patent application.

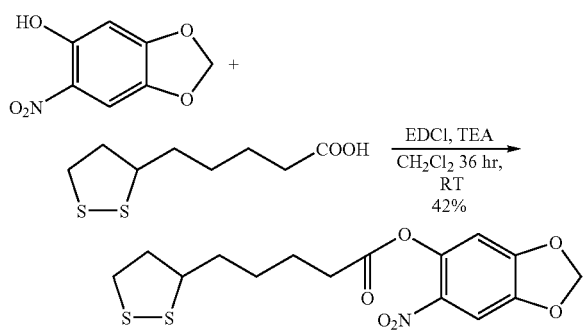

In a 100 mL round bottom flask, 0.17 g (0.001 mole) of 3,4-methylenedioxy 6-nitrophenol and 0.1 g (140 µL) (0.2 mole) of triethylamine (Aldrich, catalog #: 471283) and 50 mL of dichloromethane were stirred well for 10 minutes at room temperature. The solution became reddish orange in color. Alpha lipoic acid 0.25 g (0.0015 mole Geronova Research Inc) was added over a period of 5 minutes. N-(3-Dimethylaminopropyl)-N'-Ethylcarbodiimide hydrochloride (EDCI Aldrich, catalog #: E7750) 0.4 g (0.002 mole) was added to it for over a period of 15 minutes and continued to stir overnight. All solvents were commercial grade and purchased from Fisher Scientific. It is to be understood that other halogenated solvents may be used, including but not limited to chloroform and carbon tetrachloride. It is to be understood that other coupling agents may be used, including but not limited to dicyclocarbodiimide (DCC) and diisopropylcarbodiimide (DIC).

After about 36 hours of reaction time, thin layer chromatography (20% hexane: ethyl acetate solvent system) of the crude product was checked with the starting materials to evaluate the formation of product and disappearance of starting material 3,4-methylenedioxy 6-nitrophenol. After complete reaction, the dichloromethane was evaporated under reduced pressure. A thick yellow mass obtained which was directly purified on preparative thin layer chromatography using 20% hexane: ethyl acetate solvent system. The appropriate band was scratched out from the plate and carefully eluted with ethylacetate. A pale yellow solid was obtained and re-purified using a crystallization method. The crystallization was performed using 95% ethanol and the procedure involved slow addition of the compound (INV-7465) (about 50 mg) over a period of 5 minutes into warm ethanol (60-65 C) (about 10 mL) with continuous stirring. After complete dissolution of the compound, the resultant solution was filtered quickly and set aside for slow crystallization overnight. A yellow solid was filtered and dried using a vacuum dryer. The total yield was 42%. The crystallized product was characterized using high resolution proton NMR.

NMR characterization: The crystallized compound was characterized by high resolution proton NMR and the typical proton chemical shift values of the product are ($CDCl_3$): 7.59 (1H, singlet), 6.45 (1H, singlet), 6.15 (2H, singlet), 3.68-3.60 (1H, multiplet), 3.21-3.13 (2H, multiplet), 2.66-2.64 (2H, triplet), 2.52-2.47 (2H, multiplet), 1.97-1.92 (2H, multiplet), 1.84-1.75 (4H, multiplet), 1.74-1.58 (2H, multiplet). FIG. 1B.

Synthesis of 3,4-Methylenedioxy 6-nitro phenyl lipoate, Method-II

The alternate method of synthesizing 3,4-Methylenedioxy 6-nitro phenyl lipoate involved introducing a nitro group onto 3,4-methylenedioxylipoate and synthetic scheme is represented below. The synthesis of 3,4-methylenedioxyphenyl lipoate is presented earlier in this patent application referred as INV-7065.

In a 100 mL conical flask, 0.3 g (0.001 mole) of 3,4-methylenedioxyphenyl lipoate was

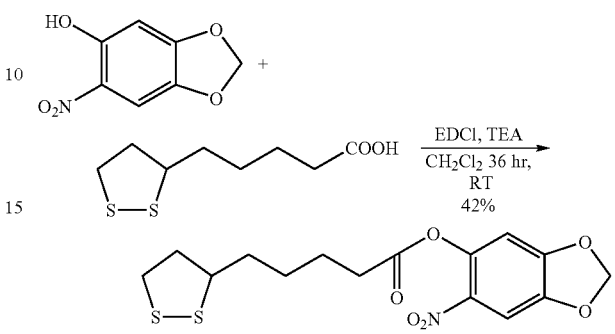

placed in 20 mL of glacial acetic acid, stirred continuously for 30 minutes at room temperature and cooled on an ice cold bath. While stirring, concentrated nitric acid (4 mL) in 10 mL glacial acetic acid was added onto the chemical mixture slowly for over a period of 45 min. The reaction mixture turned bright yellow in color and stirring continued for three hours. The resultant solution was poured directly onto the crushed ice with continuous stirring. A pale yellow semi solid settled at the bottom of the flask was extracted with dichloromethane (2×50 mL). Combined organic extracts were dried over anhydrous magnesium sulphate and solvent evaporated under reduced pressure. The resultant yellow mass was purified over preparative thin layer chromatography. The final product was repurified by recrystallization using 95% ethanol. The total yield of the reaction is 36%. The characterization was done comparing it with authentic sample by thin layer chromatography.

EXAMPLE 7

Biological Activity of 3,4-Methylenedioxy 6-nitro phenyl lipoate (also called O-Lipoyl nitromethylenedioxyphenol and INV 7465 herein)

Inhibition of Nuclear Translocation of p65 by INV 74-65: In vitro Cell Culture Experiment Cell Culture: All experiments were performed with cultured Human Umbilical Vein Endothelial Cells (HUVECs—Gibco, Invitrogen) and grown to confluence at 37° C. in a 5% $CO_2$ humidified incubator, on tissue culture flasks previously coated with 1% gelatin in supplemented culture medium (M199 with 10% heat inactivated fetal calf serum, 100 U/ml penicillin, 100 µg/ml streptomycin, 2 mM glutamine, 10 mM HEPES, pH 7.4, heparin 12 I.U./ml, 1% retinal derived growth factor, Sigma). Following trypsin treatment, the cells were detached from the flasks and final mono-layers were prepared by seeding HUVECs on gelatin-precoated culture plates and then incubated for 24-48 h to ensure confluence. Cells up to the fourth passage were used for all experiments. Recombinant human TNF-α was purchased from R&D Systems.

Human Tumor Necrosis Factor alpha (TNF α) exists as a homotrimer, consisting of three 17 kDa subunits, with a molecular mass of about 51 kDa. It is a pro-inflammatory, pro-apoptotic cytokine that regulates the activity of neutrophils, eosinophils, and T and B lymphocytes and modulates the properties of the vascular endothelium. In order to investigate the biological activity role of 3,4-Methylenedioxy 6-nitro phenyl lipoate on the inflammatory cytokine (TNF-α), an in-vitro cell culture experiment was performed.

Cell Culture: Experiments were performed with cultured Human Umbilical Vein Endothelial Cells (HUVECs—Gibco, Invitrogen) grown to confluence at 37° C. in a 5% CO2 humidified incubator, on tissue culture flasks previously coated with 1% gelatin in supplemented culture medium (M199 with 10% heat inactivated fetal calf serum, 100 U/ml penicillin, 100 ng/ml streptomycin, 2 mM glutamine, 10 mM HEPES, pH 7.4, heparin 12 U.I./ml, 1% retinal derived growth factor, Sigma). Following trypsin treatment, the cells were detached from the flasks and final monolayers were prepared by seeding HUVECs on gelatin pre-coated culture plates and then incubated for 24-48 h to ensure confluence. Cells up to the fourth passage were used for all experiments. Recombinant human TNF-α was purchased from R&D Systems.

Enzyme-Linked Immunosorbent Assay (ELISA) and results: To measure the expression of cell surface adhesion molecules, ELISA technique was utilized. Confluent HUVEC in 96-well plates were pretreated with INV-7465 at various concentrations (1 nM, 10 nM, 100 nM, 1 μM and 10 μM) for 24 hours before being stimulated with 2 ng/mL TNF-α for 6 hours. The expression of VCAM-1 and ICAM-1 were evaluated after TNF-α stimulation for 6 hours. The results of ELISA analysis of culture media after INV-7465 pre-treatment of Human HUVEC cells for 12-24 hours followed by stimulation with 2 ng/mL TNF-α for 6 hours showed marked reduction in release of VCAM and ICAM-1.

At all the concentrations tested, INV-7465 inhibited the effects of the pro-inflammatory cytokine, TNF-α, which was observed as a decrease in the ratio of nuclear to cytoplasmic staining of p65. 3,4-Methylenedioxy 6-nitro phenyl lipoate (INV-7465) had potent anti-inflammatory effects and antagonized the effects of the inflammatory molecule TNF-α.

EXAMPLE 8

Treatment of a Cardiovascular Patient

A 55 year old man presents with uncomfortable pressure, squeezing and pain in the center of his chest as well as in shoulders, arms, neck, jaw and back. He shows other symptoms of shortness of breath and elevated blood pressure. After being evaluated with an angiography, he is diagnosed as suffering from atherosclerosis with plaque formation in the coronary arteries. The patient is administered a composition comprising an effective amount of 3,4-methylenedioxy-6-nitrophenyl acetate (INV 75) (1.0 to 100-mg/kg). Alternate therapies include, 3,4-methylenedioxy phenyl acetate (INV 73); 3,4-methylenedioxy-6-nitrophenol (INV 74; 3,4-Methylenedioxy 6-nitro phenyl lipoate (INV-7465) or 3,4-Methylenedioxy phenyl lipoate (INV-7065). The composition is optionally administered in conjunction with therapy such as administration of aspirin, a drug to reduce the tendency of platelet aggregation, such as clopidogrel bisulfate, a statin, an angiotensin converting enzyme inhibitor, and/or heparin or a combination thereof, using dosages known to one of ordinary skill in the art. Patient reports improvement in the chest pain, shortness of breath. He is again evaluated with an angiography to measure reduced plaque in his arteries.

EXAMPLE 9

Treatment of a Cardiovascular Patient With Chest Pain (Angina)

A 55 year old man presents with uncomfortable pressure, squeezing and pain in the center of his chest for less than 30 minutes. He is taken to the cardiac angiography suite for suspected unstable angina. He shows other symptoms of shortness of breath and irregular heartbeat. After being evaluated with an angiography, he is diagnosed as suffering from atherosclerosis with plaque formation in the coronary arteries. The patient is administered a composition comprising an effective amount of 3,4-Methylenedioxy phenyl lipoate (INV-7065) (1.0 to 100 mg/kg). The composition is optionally administered in conjunction with therapy such as administration of aspirin, a drug to reduce the tendency of platelet aggregation, such as clopidogrel bisulfate, a statin, ezetimibe, lipoic acid, an angiotensin converting enzyme inhibitor, and/or heparin or a combination thereof, using dosages known to one of ordinary skill in the art. Patient reports improvement in the chest-pain, shortness of breath. He is again evaluated with an angiography to measure reduced plaque in his arteries.

EXAMPLE 10

Treatment of a Cardiovascular Patient With Chest Pain (Angina)

A 55 year old man presents with uncomfortable pressure, squeezing and pain in the center of his chest for less than 30 minutes. He is taken to the cardiac angiography suite for suspected unstable angina. He shows other symptoms of shortness of breath and irregular heartbeat. After being evaluated with an angiography, he is diagnosed as suffering from atherosclerosis with plaque formation in the coronary arteries. The patient is administered a composition comprising an effective amount of 3,4-Methylenedioxy phenyl lipoate (INV-7465) (1.0 to 100 mg/kg). The composition is optionally administered in conjunction with therapy such as administration of aspirin, a drug to reduce the tendency of platelet aggregation, such as clopidogrel bisulfate, a statin, ezetimibe, lipoic acid, an angiotensin converting enzyme inhibitor, and/or heparin or a combination thereof, using dosages known to one of ordinary skill in the art. Patient reports improvement in the chest pain, shortness of breath. He is again evaluated with an angiography to measure reduced plaque in his arteries.

EXAMPLE 11

Treatment of a Cardiovascular Patient With Acute Non-ST Elevation Myocardial Infarction A 55 year old man presents with uncomfortable pressure, squeezing and pain in the center of his chest as well as in shoulders, arms, neck, jaw and back for over 4 hours. He also complains of shortness of breath. He is evaluated in the emergency room and found to have elevation in Troponin I and his EKG demonstrates changes consistent with myocardial ischemia. He is given aspirin, clopidogrel, nitrates and IV heparin and taken to the catheterization laboratory. After being evaluated with an angiography, he is diagnosed as suffering from a <90% blockage in the left anterior descending coronary artery. The patient is administered a composition comprising an effective amount of 3,4-Methylenedioxy 6-nitro phenyl lipoate (INV-7465) (1.0 to 100 mg/kg) in the catheterization laboratory. Patient reports improvement in the chest pain, shortness of breath. He is again evaluated with an angiography to measure reduced plaque in his arteries.

EXAMPLE 12

Treatment of a Cardiovascular Patient With Acute Non-ST Elevation Myocardial Infarction A 55 year old man presents with uncomfortable pressure, squeezing and pain in the center of his chest as well as in shoulders, arms, neck, jaw and back for over 4 hours. He also complains of shortness of breath. He is evaluated in the emergency room and found to have elevation in Troponin I and his EKG demonstrates changes consistent with myocardial ischemia. He is given aspirin, clopidogrel, nitrates and IV heparin and taken to the catheterization laboratory. After being evaluated with an angiography, he is diagnosed as suffering from a <90% blockage in the left anterior descending coronary artery. The patient is administered a composition comprising an effective amount of INV-75 (1.0 to 100 mg/kg) in the catheterization laboratory. Patient reports improvement in the chest pain, shortness of breath. He is again evaluated with an angiography to measure reduced plaque in his arteries.

EXAMPLE 13

Treatment of a Patient with an Acute ST Elevation Myocardial Infarction

A 50-year old man presents with sudden chest pain typically radiating to the left arm or left side of the neck, shortness of breath, nausea and palpitation with vomiting and sweating. After being evaluated with an electrocardiogram (EKG, ECG), a chest X-ray and blood tests to detect elevations in cardiac markers (blood tests to detect heart muscle damage), he is diagnosed as suffering from acute ST elevation myocardial infarction. The patient is administered a composition comprising an effective amount of 3,4-methylenedioxy-6-nitrophenyl acetate (INV 75) (1.0 to 100 mg/kg) intravenously. The composition is optionally administered in conjunction with therapy such as thrombolytic drugs such as tissue plasminogen activator (tPA) or streptokinase and administration of aspirin, a drug to reduce the tendency of platelet aggregation, such as clopidogrel bisulfate, a statin, and/or heparin or a combination thereof, using dosages known to one of ordinary skill in the art. Patient reports improvement in the chest pain, shortness of breath and palpitations.

EXAMPLE 14

Treatment of a Patient with an Acute ST Elevation Myocardial Infarction

A 50-year old man presents with sudden chest pain typically radiating to the left arm or left side of the neck, shortness of breath, nausea and palpitation with vomiting and sweating. After being evaluated with an electrocardiogram (EKG, ECG), a chest X-ray and blood tests to detect elevations in cardiac markers (blood tests to detect heart muscle damage), he is diagnosed as suffering from acute ST elevation myocardial infarction. The patient is administered a composition comprising an effective amount of 3,4-methylenedioxy-6-nitrophenyl acetate (INV 7465) (1.0 to 100 mg/kg) intravenously. The composition is optionally administered in conjunction with therapy such as thrombolytic drugs such as tissue plasminogen activator (tPA) or streptokinase and administration of aspirin, a drug to reduce the tendency of platelet aggregation, such as clopidogrel bisulfate, a statin, and/or heparin or a combination thereof, using dosages known to one of ordinary skill in the art. Patient reports improvement in the chest pain, shortness of breath and palpitations.

EXAMPLE 15

Treatment of a Patient with an Acute ST Elevation Myocardial Infarction

A 50-year old man presents with sudden chest pain typically radiating to the left arm or left side of the neck, shortness of breath, nausea and palpitation with vomiting and sweating. After being evaluated with an electrocardiogram (EKG, ECG), a chest X-ray and blood tests to detect elevations in cardiac markers (blood tests to detect heart muscle damage), he is diagnosed as suffering from acute ST elevation myocardial infarction. The patient is administered a composition comprising an effective amount of 3,4-methylenedioxy-6-nitrophenyl acetate (INV 7065) (1.0 to 100 mg/kg) intravenously. The composition is optionally administered in conjunction with therapy such as thrombolytic drugs such as tissue plasminogen activator (tPA) or streptokinase and administration of aspirin, a drug to reduce the tendency of platelet aggregation, such as clopidogrel bisulfate, a statin, and/or heparin or a combination thereof, using dosages known to one of ordinary skill in the art. Patient reports improvement in the chest pain, shortness of breath and palpitations.

EXAMPLE 16

Treatment of a Patient with Recent Myocardial Infarction (Secondary Prevention)

A 50-year old man presents with sudden chest pain typically radiating to the left arm or left side of the neck, shortness of breath, nausea and palpitation with vomiting and sweating. After being evaluated with an electrocardiogram (EKG, ECG), a chest X-ray and blood tests to detect elevations in cardiac markers (blood tests to detect heart muscle damage), he is diagnosed as suffering from myocardial infarction. The patient is administered therapy such as aspirin, a drug to reduce the tendency of platelet aggregation, such as clopidogrel bisulfate, a statin, IV heparin and taken to the catheterization laboratory where he undergoes stenting of the coronary artery. He is allowed to recover for a 12-24 hour period. Oral therapy with 3,4-methylenedioxy-6-nitrophenyl acetate (INV 75) (1.0 to 100 mg/kg) is started and continued for at least a year. During the follow-up visit a month later, patient reports improvement in symptoms.

EXAMPLE 17

Treatment of a Patient with Recent Myocardial Infarction (Secondary Prevention)

A 50-year old man presents with sudden chest pain typically radiating to the left arm or left side of the neck, shortness of breath, nausea and palpitation with vomiting and sweating. After being evaluated with an electrocardiogram (EKG, ECG), a chest X-ray and blood tests to detect elevations in cardiac markers (blood tests to detect heart muscle damage), he is diagnosed as suffering from myocardial infarction. The patient is administered therapy such as aspirin, a drug to reduce the tendency of platelet aggregation, such as clopidogrel bisulfate, a statin, IV heparin and taken to the catheterization laboratory where he undergoes stenting of the coronary artery. He is allowed to recover for a 12-24 hour period. Oral therapy with 3,4-methylenedioxy-6-nitrophenyl acetate (INV 7065) (1.0 to 100 mg/kg) is started and continued for at least a year. During the follow-up visit a month later, patient reports improvement in symptoms.

EXAMPLE 18

Treatment of a Patient with Recent Myocardial Infarction (Secondary Prevention)

A 50-year old man presents with sudden chest pain typically radiating to the left arm or left side of the neck, shortness of breath, nausea and palpitation with vomiting and sweating. After being evaluated with an electrocardiogram (EKG, ECG), a chest X-ray and blood tests to detect elevations in cardiac markers (blood tests to detect heart muscle damage), he is diagnosed as suffering from myocardial infarction. The patient is administered therapy such as aspirin, a drug to reduce the tendency of platelet aggregation, such as clopidogrel bisulfate, a statin, IV heparin and taken to the catheterization laboratory where he undergoes stenting of the coronary artery. He is allowed to recover for a 12-24 hour period. Oral therapy with 3,4-methylenedioxy-6-nitrophenyl acetate (INV-7465) (1.0 to 100 mg/kg) is started and continued for at least a year. During the follow-up visit a month later, patient reports improvement in symptoms.

EXAMPLE 19

Treatment of a Patient with Chronic Myocardial Infarction (Secondary Prevention)

A 50-year old man with a prior history of a heart attack (myocardial infarction) 1 year ago presents for evaluation. He is asymptomatic. The patient is administered a composition comprising an effective amount of 3,4-Methylenedioxy 6-nitro phenyl lipoate (INV-7465) (1.0 to 100 mg/kg). Alternate therapies include, 3,4-methylenedioxy phenyl acetate (INV 73); 3,4-methylenedioxy-6-nitrophenol (INV 74); 3,4-methylenedioxy-6-nitrophenyl acetate (INV 75); 3,4-Methylenedioxy 6-nitro phenyl lipoate (INV-7465) or 3,4-Methylenedioxy phenyl lipoate (INV-7065). The composition is administered in conjunction with therapy such as aspirin, a drug to reduce the tendency of platelet aggregation, such as clopidogrel bisulfate, a statin, ezetimibe, an angiotensin converting enzyme inhibitor or angiotensin receptor blocker, and other anti-hypertensive agents such as beta-blockers, using dosages known to one of ordinary skill in the art. Patient notes added benefit in total and LDL cholesterol and a reduction in inflammatory markers such as C reactive protein.

EXAMPLE 20

Treatment of a Patient with Chronic Myocardial Infarction with Chronic Stable Angina A 50-year old man with a prior history of a heart attack (myocardial infarction) 10 years ago presents for evaluation. He is complaining of anginal chest pains that are relived with one sub-lingual nitroglycerin and has had these pains chronically. The patient is administered a composition comprising an effective amount of oral 3,4-Methylenedioxy 6-nitro phenyl lipoate (INV-7465) (1.0 to 100 mg/kg). Alternate therapies include, 3,4-methylenedioxy phenyl acetate (INV 73); 3,4-methylenedioxy-6-nitrophenol (INV 74); 3,4-methylenedioxy-6-nitrophenyl acetate (INV 75); or 3,4-Methylenedioxy phenyl lipoate (INV-7065). Patient notes added benefit in his chest pains with this regimen after taking the medication for two weeks.

EXAMPLE 21

Administration of the Compounds of the Present Invention to Treat Established Atherosclerosis in Humans Individuals with established atherosclerosis with evidence of plaque in the coronary arteries, carotid arteries or peripheral arteries are known to be at risk for future cardiovascular events such as heart attacks and strokes. These individuals are on treatments such as statins and anti-hypertensive agents such as ACE inhibitors, diuretics or calcium channel blockers. They also will receive an acceptable dose of a composition comprising a compound of the present invention in an acceptable carrier orally and chronically for durations in excess of 12 months. In one study, 3,4-methylenedioxy phenyl acetate (INV 73); 3,4-methylenedioxy-6-nitrophenol (INV 74); 3,4-methylenedioxy-6-nitrophenyl acetate (INV 75); 3,4-Methylenedioxy 6-nitro phenyl lipoate (INV-7465) or 3,4-Methylenedioxy phenyl lipoate (INV-7065) are administered to these individuals. A repeat IVUS measurement is made at the end of the treatment period to assess the effect of the infusion of the composition on coronary atherosclerosis in the target vessel. Plaque is reduced in the atherosclerotic coronary artery following the treatment demonstrating efficacy of these compounds of the present invention to treat atherosclerosis.

EXAMPLE 22

Administration of the Compounds of the Present Invention to Treat Atherosclerosis in Humans (Primary Prevention)

Individuals with risk factors for atherosclerosis such as family history, hypertension and high cholesterol are known to be at risk for future cardiovascular events such as heart attacks and strokes. These individuals are on primary prevention treatments such as hypolipidemic drug therapy such as statins aspirin and anti-hypertensive agents such as ACE inhibitors, diuretics or calcium channel blockers. They also will receive an acceptable dose of a composition comprising a compound of the present invention in an acceptable carrier orally chronically for durations in excess of 12 months. In one study, 3,4-methylenedioxy phenyl acetate (INV 73); 3,4-methylenedioxy-6-nitrophenol (INV 74); 3,4-methylenedioxy-6-nitrophenyl acetate (INV 75); 3,4-Methylenedioxy 6-nitro phenyl lipoate (INV-7465) or 3,4-Methylenedioxy phenyl lipoate (INV-7065) are administered to these individuals. A repeat IVUS measurement is made at the end of the treatment period to assess the effect of the infusion of the composition on coronary atherosclerosis in the target vessel. Plaque is reduced in the atherosclerotic coronary artery following the treatment demonstrating efficacy of these compounds of the present invention to treat atherosclerosis.

EXAMPLE 23

Administration of the Compounds of the Present Invention to Prevent or Delay the Onset of Atherosclerosis in Humans Individuals with documented risk factors for atherosclerosis and having high plasma cholesterol levels have a ultrasound analysis of the coronary (IVUS), carotid (IMT) or popliteal arteries to establish a baseline measurement. A portion of these individuals are daily administered a composition comprising a compound of the present invention in an acceptable carrier at a dose of 2 mg/kg to 50 mg/kg intravenously (iv) or intramuscular (im) 1 to 3 times per week over a period of approximately one to six months. The following compounds are administered to these individuals: 3,4-methylenedioxy phenyl acetate (INV 73); 3,4-methylenedioxy-6-nitrophenol (INV 74); 3,4-methylenedioxy-6-nitrophenyl acetate (INV 75); 3,4-Methylenedioxy 6-nitro phenyl lipoate (INV-7465) or 3,4-Methylenedioxy phenyl lipoate (INV-7065).

The other individuals receive the carrier alone. A new ultrasound analysis at the end of the treatment period indicates higher levels of plaque in the vessels of individuals receiving the carrier. This example indicates that the individual compounds of the present invention are effective in preventing or reducing atherosclerosis in individuals at risk for developing atherosclerosis and in reducing plaque accumulation in coronary, carotid or popliteal arteries.

EXAMPLE 24

Administration of the Compounds of the Present Invention to Treat Patients with Type I and Type II Diabetics Individuals with Type I and Type II diabetes are at risk for future cardiovascular events such as heart attacks, strokes and kidney disease. These individuals are on prevention treatments such as hypolipidemic drug therapy such as statins and anti-hypertensive agents such as ACE inhibitors. They are already receiving glycemia lowering strategies such as Insulin, PPARγ agents, Metformin or sulfonylurea therapy. They also will receive an acceptable dose of a composition comprising a compound of the present invention in an acceptable carrier orally chronically for durations in excess of 12 months. In one study, 3,4-Methylenedioxy 6-nitro phenyl lipoate (INV-7465) or 3,4-Methylenedioxy phenyl lipoate (INV-7065) are administered to these individuals. The patients undergo the following measurements: HbA1C to assess glycemic control, urinary microalbuminura, blood pressure and lipid measurements. At the end of 12 months of treatment, there is lowering of HbA1C and urinary microalbuminuria. There is an improvement in VLDL cholesterol and a decrease in triglycerides with any of these treatments [(3,4-methylenedioxy phenyl acetate (INV 73); 3,4-methylenedioxy-6-nitrophenol (INV 74); 3,4-methylenedioxy-6-nitrophenyl acetate (INV 75); 3,4-Methylenedioxy 6-nitro phenyl lipoate (INV-7465) or 3,4-Methylenedioxy phenyl lipoate (INV-7065)].

EXAMPLE 25

Administration of the Compounds of the Present Invention to Treat Dyslipidemia in Patients with Type I and Type II Diabetics Individuals with Type I and Type II diabetes are at risk for future cardiovascular events such as heart attacks, strokes and kidney disease. These individuals often have abnormalities in lipids such as elevations in triglycerides and VLDL cholesterol. They are on treatments such as hypolipidemic drug therapy such as statins and fibrates (Gemfibrozil or Fenofibrate) to lover cholesterol levels in conjunction with glycemia lowering strategies such as Insulin, PPAR γ agents, Metformin or sulfonylurea therapy. In addition to these treatments they will also receive an acceptable dose of a composition comprising a compound of the present invention in an acceptable carrier orally chronically for durations in excess of 12 months. In one study, (3,4-methylenedioxy phenyl acetate (INV 73); 3,4-methylenedioxy-6-nitrophenol (INV 74); 3,4-methylenedioxy-6-nitrophenyl acetate (INV 75); are administered to these individuals. The patients undergo lipid measurements at baseline and at the end of treatment for a 12 month duration. At the end of 12 months of treatment, there is lowering of VLDL cholesterol and a decrease in triglycerides.

EXAMPLE 26

Administration of the Compounds of the Present Invention to Treat Inflammatory Arthritis Individuals with rheumatoid arthritis, psoriatic arthritis and systemic lupus erythematosis suffer from recurrent bouts of inflammatory arthritis. They are usually on treatments such as non-steroidal agents such as cyclooxygenase inhibitors, anti-TNFα treatments and other types of immunotherapy. In addition to these treatments they will also receive an acceptable dose of a composition comprising a compound of the present invention in an acceptable carrier orally chronically for durations in excess of 6 months. In one study, 3,4-methylenedioxy-6-nitrophenyl acetate (INV 75) is administered to these individuals. The patients undergo an assessment of joint pains and inflammatory markers such as C-reactive protein (CRP) and erythrocyte sedimentation rate. At the end of 6 months of treatment, there is marked improvement in joint pains and markers of inflammation.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

What is claimed is:

1. A compound consisting of: 3,4-methylenedioxyphenyl lipoate (INV-7065):

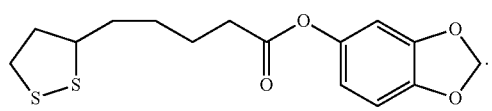

2. The compound consisting of 3,4-methylenedioxy 6-nitrophenyl lipoate (INV-7465):

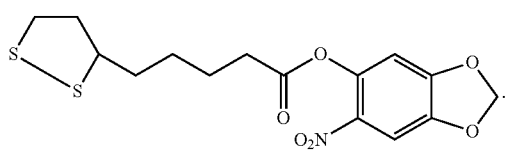

3. The compound consisting of:

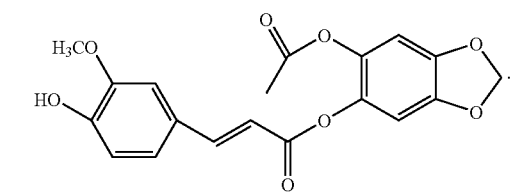

4. The compound consisting of:

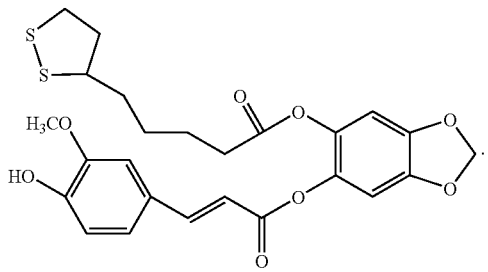

5. The compound consisting of:
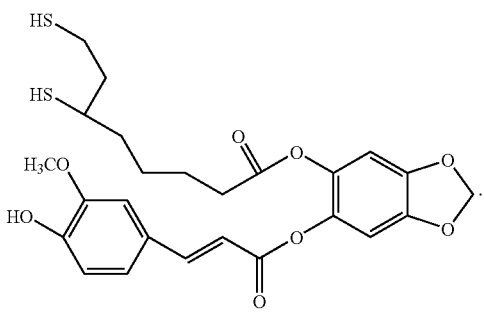
6. The compound consisting of:
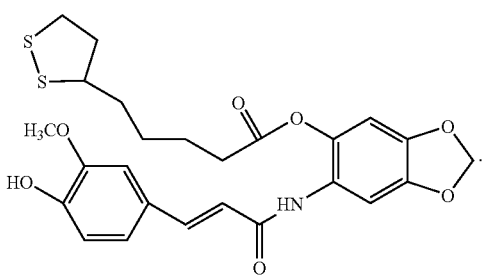
7. The compound consisting of:
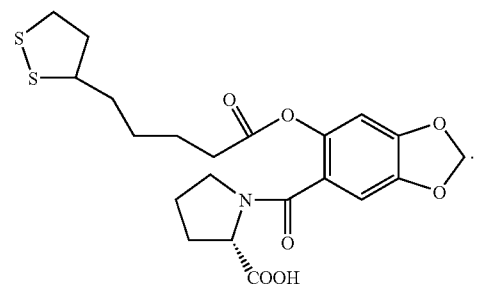
8. The compound consisting of:
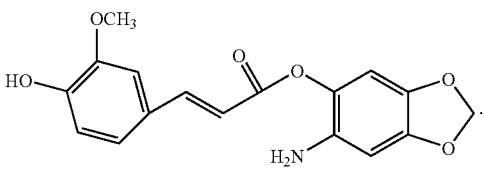
9. The compound consisting of:
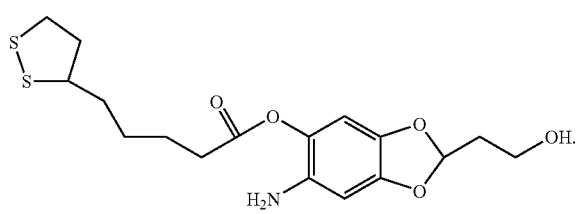
10. The compound consisting of:
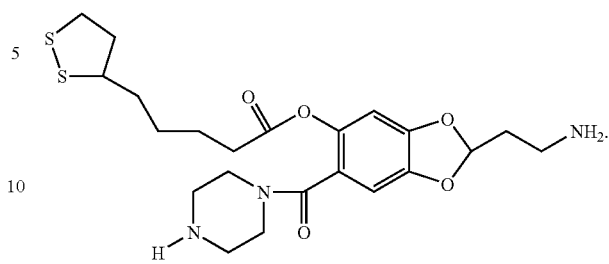
11. The compound consisting of:
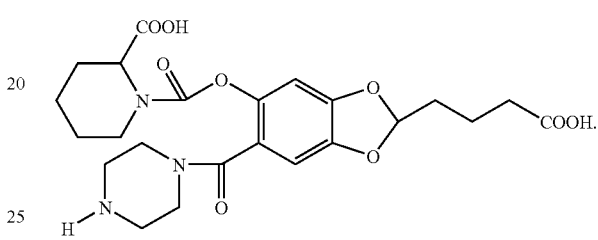
12. The compound consisting of:
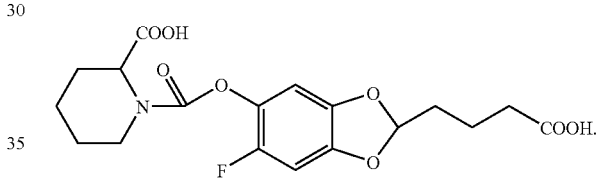
13. The compound consisting of:
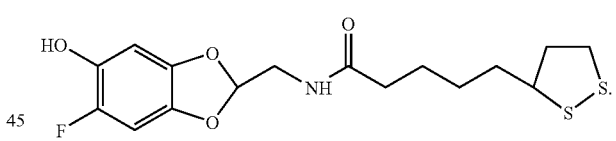
14. The compound consisting of:
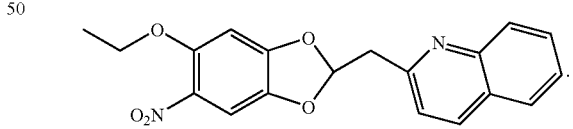
15. The compound consisting of:
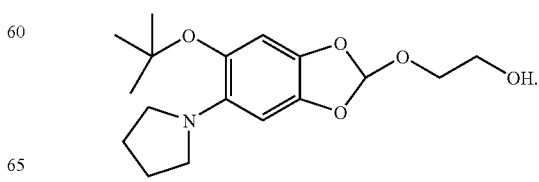

16. The compound consisting of:

[chemical structure]

17. A composition comprising a compound of any one of claims 1 to 16, and a pharmaceutically acceptable carrier.

18. A composition comprising a compound of any one of claims 1 to 16, further including one or more therapeutic compounds selected from: a lipoic acid, an HMG-CoA reductase inhibitor, an angiotensin converting enzyme inhibitor, a fat uptake inhibitor, an angiotensin receptor blocker, a PPARα agonist, a PPARγ agonists, acetylsalicylic acid, an inhibitor of platelet aggregation, a cholesteryl ester transfer protein inhibitor, a thiazolidinedione, niacin, a fibrate, an inhibitor of clot formation or a beta-blocker, or a combination thereof.

19. A method of treating or preventing cardiovascular disease, vascular disease, inflammatory disease, and Type I and Type II diabetes and dyslipidemia patients at risk for hypertension, stroke, cardiovascular and renal disease in a patient any one of claims 1 to 16,
wherein administering the composition treats or prevents cardiovascular disease, vascular disease, inflammatory disease, and Type I and Type II diabetes and dyslipidemia patients at risk for hypertension, stroke, cardiovascular and renal disease in the patient.

20. The method of claim 19, wherein $R_1$ is hydrogen and $R_2$ is $N_2O$ or is absent.

21. The method of claim 19, wherein $R_1$ is acetyl and $R_2$ is $N_2O$ or is absent.

22. The method of claim 19, wherein $R_1$ is lipoyl and $R_2$ is $N_2O$ or is absent.

23. The method of claim 19, wherein the compound is:
3,4-methylenedioxyphenyl acetate (INV-73),
3,4-methylenedioxy-6-nitrophenol (INV-74),
3,4-methylenedioxy-6-nitrophenyl acetate (INV-75),
3,4-methylenedioxyphenyl lipoate (INV-7065), or
3,4-methylenedioxy 6-nitrophenyl lipoate (INV-7465).

24. The method of claim 19, further comprising administering a lipoic acid, an HMG-CoA reductase inhibitor, an angiotensin converting enzyme inhibitor, a fat uptake inhibitor, an angiotensin receptor blocker, a PPAR-alpha agonist, a PPAR-gamma agonists, acetylsalicylic acid, an inhibitor of platelet aggregation, a cholesteryl ester transfer protein inhibitor, a thiazolidinedione, niacin, a fibrate, an inhibitor of clot formation or a beta-blocker, or a combination thereof.

25. A method of making 3,4-methylenedioxyphenyl lipoate (INV-7065) comprising the sequential steps of:
mixing dimethylamino pyridine, and 3,4-methylenedioxyphenol with halogenated solvent under nitrogen atmosphere to form a mixture;
adding alpha lipoic acid to the mixture;
adding a coupling reagent to the mixture;
stirring the mixture; and,
removing the halogenated solvent.

26. A method of making 3,4-methylenedioxy 6-nitrophenyl lipoate (INV-7465) comprising the sequential steps of:
mixing triethylamine and 3,4-methylenedioxy 6-nitrophenol with halogenated solvent to form a mixture;
adding alpha lipoic acid to the mixture;
adding a coupling reagent to the mixture;
stirring the mixture; and,
removing the halogenated solvent.

27. The method of claim 25, further comprising purifying the 3,4-methylenedioxyphenyl lipoate (INV-7065).

28. The method of claim 26, further comprising purifying the 3,4-methylenedioxy 6-nitrophenyl lipoate (INV-7465).

29. A method for treating a subject in need thereof, comprising:
administering to the subject in need of such treatment an agent that modulates expression of a p65 subunit of NF-κB, in an amount effective to treat the cardiovascular disease, wherein the agent comprising a compound of any one of claims 1 to 16.

30. A composition for increasing LDL receptor expression in a subject in need thereof, comprising an effective amount of 3,4-methylenedioxy-6-nitrophenyl acetate, or a pharmacologically active analog thereof.

31. A composition for increasing PPAR-alpha ligand binding activity in a selective fashion without effects on PPARα or PPARγ, in a subject in need thereof, comprising an effective amount of 3,4-methylenedioxy-6-nitrophenyl acetate, or a pharmacologically active analog thereof.

32. A dietary supplement comprising an effective amount of 3,4-methylenedioxy-6-nitrophenyl acetate sufficient to in ameliorate cardiac, vascular, inflammatory, Types I and II diabetes and/or dyslipidemia symptoms in a subject in need thereof.

33. A composition for slowing of the rate of progression of plaque in a subject in need thereof, comprising:
an effective amount of 3,4-methylenedioxy-6-nitrophenyl acetate, or a pharmacologically active analog thereof.

34. A composition for inhibiting macrophage infiltration in a subject in need thereof, comprising:
an effective amount of 3,4-methylenedioxy-6-nitrophenyl acetate, or a pharmacologically active analog thereof.

35. A composition for increasing smooth muscle content in a subject in need thereof, comprising:
an effective amount of 3,4-methylenedioxy-6-nitrophenyl acetate, or a pharmacologically active analog thereof.

36. A composition for increasing LDL clearance through an increase in LDL receptor expression in a subject in need thereof, comprising:
an effective amount of 3,4-methylenedioxy-6-nitrophenyl acetate, or a pharmacologically active analog thereof.

37. A composition for decreasing aortic contraction by angiotensin II in a subject in need thereof, comprising:
an effective amount of 3,4-methylenedioxy-6-nitrophenyl acetate, or a pharmacologically active analog thereof.

38. A composition for modulating acetylcholine dependent vasodilation in a subject in need thereof, comprising:
an effective amount of 3,4-methylenedioxy-6-nitrophenyl acetate, or a pharmacologically active analog thereof.

39. An anti-inflammatory composition, comprising:
an effective amount of 3,4-methylenedioxy-6-nitrophenyl acetate, or a pharmacologically active analog thereof.

40. A composition for attenuating plaque burden in a subject in need thereof, comprising:
an effective amount of the compound of claim 1 (INV-7065), or a pharmacologically active analog thereof.

41. A composition for decreasing vascular contractility to an alpha receptor agonist and/or increasing vascular insulin sensitivity in a subject in need thereof, comprising:
an effective amount of the compound of claim 1 (INV-7065), or a pharmacologically active analog thereof.

42. A composition for reducing lipid deposition in an aortic wall in a subject in need thereof, comprising an effective amount of the compound of claim 1 (INV-7065), or a pharmacologically active analog thereof.

43. A composition for decreasing triglyceride (TG) levels in a subject in need thereof, comprising:
 an effective amount of the compound of claim 1 (INV-7065), or a pharmacologically active analog thereof.

44. An anti-inflammatory composition comprising an effective amount of at least one compound of claim 1, or a pharmacologically active analog thereof.

45. A pharmaceutical composition for the treatment of human aortic plaque formation in a subject in need thereof, comprising:
 at least one compound of claim 1, and a pharmaceutically acceptable carrier.

* * * * *